United States Patent
Arne et al.

(10) Patent No.: US 9,439,566 B2
(45) Date of Patent: Sep. 13, 2016

(54) RE-WEARABLE WIRELESS DEVICE

(71) Applicant: Proteus Digital Health, Inc., Redwood City, CA (US)

(72) Inventors: Lawrence Arne, Palo Alto, CA (US); Todd Thompson, San Jose, CA (US); Timothy Robertson, Belmont, CA (US); Robert Azevedo, Albany, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 463 days.

(21) Appl. No.: 13/841,797

(22) Filed: Mar. 15, 2013

(65) Prior Publication Data

US 2014/0051946 A1     Feb. 20, 2014

(51) Int. Cl.
*A61B 5/00* (2006.01)
*H04W 40/24* (2009.01)
(Continued)

(52) U.S. Cl.
CPC ........... *A61B 5/0022* (2013.01); *A61B 5/0006* (2013.01); *A61B 5/0028* (2013.01); *A61B 5/0404* (2013.01); *A61B 5/053* (2013.01); *A61B 5/073* (2013.01); *G06F 19/3418* (2013.01);
(Continued)

(58) Field of Classification Search
CPC .... A61B 5/6833; A61B 5/0002; A61B 5/02; A61B 2560/0412; A61B 2560/0443; A61B 2560/0456; H01R 13/627; G06F 19/3418
See application file for complete search history.

(56) References Cited

U.S. PATENT DOCUMENTS 3,340,866 A   9/1967 Noller
3,607,788 A   9/1971 Adolph
(Continued)

FOREIGN PATENT DOCUMENTS

CN    1588649    3/2005
CN    1991868    7/2007
(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.
(Continued)

*Primary Examiner* — Bill Thomson
*Assistant Examiner* — Marie Archer
(74) *Attorney, Agent, or Firm* — K&L Gates LLP

(57) ABSTRACT

A re-wearable wireless device includes a reusable component to be secured to a disposable component. The reusable component includes a sensor interface to receive signals from an electrode secured to a living subject and monitors physiological and physical parameters associated with the living subject and a cellular wireless communication circuit. An adhesive base the device includes a first adhesive layer and a second adhesive layer partially covering the first adhesive layer around a perimeter thereof, where the first and second adhesive layers include different adhesives. A method of establishing a link between two wireless devices is also disclosed, where a first wireless device with an insignia representing a communication channel address identification is provided. An image of the insignia is captured with a mobile telephone computing device comprising an image sensor. The captured image is processed to extract the communication channel address identification represented by the insignia.

14 Claims, 10 Drawing Sheets

(51) Int. Cl.

| | | |
|---|---|---|
| *H04B 13/00* | (2006.01) | |
| *G06F 19/00* | (2011.01) | |
| *A61B 5/07* | (2006.01) | |
| *A61B 5/0404* | (2006.01) | |
| *A61B 5/053* | (2006.01) | |
| *A61B 5/0205* | (2006.01) | |
| *A61B 5/0408* | (2006.01) | |
| *A61B 5/0428* | (2006.01) | |
| *A61B 5/11* | (2006.01) | |
| *A61B 5/145* | (2006.01) | |

(52) U.S. Cl.
CPC ............ *H04B 13/005* (2013.01); *H04W 40/24* (2013.01); *A61B 5/02055* (2013.01); *A61B 5/0428* (2013.01); *A61B 5/04085* (2013.01); *A61B 5/11* (2013.01); *A61B 5/1112* (2013.01); *A61B 5/145* (2013.01); *A61B 5/14532* (2013.01); *A61B 2560/0209* (2013.01); *A61B 2560/0412* (2013.01); *A61B 2560/0468* (2013.01); *A61B 2562/0219* (2013.01)

(56) References Cited

U.S. PATENT DOCUMENTS

| | | |
|---|---|---|
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,828,766 A | 8/1974 | Krasnow |
| 3,837,339 A | 9/1974 | Aisenberg et al. |
| 3,989,050 A | 11/1976 | Buchalter |
| 4,067,014 A | 1/1978 | Wheeler et al. |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,121,573 A | 10/1978 | Crovella et al. |
| 4,129,125 A | 12/1978 | Lester |
| 4,166,453 A | 9/1979 | McClelland |
| 4,185,172 A | 1/1980 | Melindo et al. |
| 4,239,046 A | 12/1980 | Ong |
| 4,269,189 A | 5/1981 | Abraham |
| 4,331,654 A | 5/1982 | Morris |
| 4,333,150 A | 6/1982 | Matty et al. |
| 4,345,588 A | 8/1982 | Widder et al. |
| 4,418,697 A | 12/1983 | Tama |
| 4,425,117 A | 1/1984 | Hugemann |
| 4,494,950 A | 1/1985 | Fischell |
| 4,513,385 A | 4/1985 | Muir |
| 4,559,950 A | 12/1985 | Vaughan |
| 4,578,061 A | 3/1986 | Lemelson |
| 4,635,641 A | 1/1987 | Hoffman |
| 4,654,165 A | 3/1987 | Eisenber |
| 4,669,479 A | 6/1987 | Dunseath |
| 4,725,997 A | 2/1988 | Urquhart et al. |
| 4,749,575 A | 6/1988 | Rotman et al. |
| 4,763,659 A | 8/1988 | Dunseath |
| 4,784,162 A | 11/1988 | Ricks |
| 4,793,825 A | 12/1988 | Benjamin et al. |
| 4,809,705 A | 3/1989 | Ascher |
| 4,844,076 A | 7/1989 | Lesho |
| 4,858,617 A | 8/1989 | Sanders |
| 4,896,261 A | 1/1990 | Nolan |
| 4,975,230 A | 12/1990 | Pinkhasov |
| 4,987,897 A | 1/1991 | Funke |
| 5,016,634 A | 5/1991 | Vock et al. |
| 5,079,006 A | 1/1992 | Urquhart |
| 5,113,859 A | 5/1992 | Funke |
| 5,167,626 A | 12/1992 | Casper |
| 5,176,626 A | 1/1993 | Soehendra |
| 5,232,383 A * | 8/1993 | Barnick ............ A61N 1/048 439/855 |
| 5,245,332 A | 9/1993 | Katzenstein et al. |
| 5,261,402 A | 11/1993 | DiSabito |
| 5,263,481 A | 11/1993 | Axelgaard et al. |
| 5,281,287 A | 1/1994 | Lloyd |
| 5,283,136 A | 2/1994 | Peled et al. |
| 5,318,557 A | 6/1994 | Gross |
| 5,394,882 A | 3/1995 | Mawhinney |
| 5,458,141 A | 10/1995 | Neil et al. |
| 5,485,841 A | 1/1996 | Watkin et al. |
| 5,511,548 A | 4/1996 | Riazzi et al. |
| 5,551,020 A | 8/1996 | Flax et al. |
| 5,596,302 A | 1/1997 | Mastrocola et al. |
| D377,983 S | 2/1997 | Sabri et al. |
| 5,634,466 A | 6/1997 | Gruner |
| 5,634,468 A | 6/1997 | Platt |
| 5,645,063 A | 7/1997 | Straka et al. |
| 5,720,771 A | 2/1998 | Snell |
| 5,724,432 A | 3/1998 | Bouvet et al. |
| 5,740,811 A | 4/1998 | Hedberg |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach |
| 6,081,734 A | 6/2000 | Batz |
| 6,095,985 A | 8/2000 | Raymond et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,200,265 B1 | 3/2001 | Walsh et al. |
| 6,200,625 B1 | 3/2001 | Beckett |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,238,338 B1 | 5/2001 | DeLuca et al. |
| 6,245,057 B1 | 6/2001 | Sieben et al. |
| 6,275,476 B1 | 8/2001 | Wood |
| 6,285,897 B1 | 9/2001 | Kilcoyne et al. |
| 6,287,252 B1 | 9/2001 | Lugo |
| 6,289,238 B1 | 9/2001 | Besson et al. |
| 6,301,298 B1 | 10/2001 | Kuntz et al. |
| 6,315,719 B1 | 11/2001 | Rode et al. |
| 6,317,714 B1 | 11/2001 | Del Castillo |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,526,315 B1 | 2/2003 | Inagawa |
| 6,544,174 B2 | 4/2003 | West |
| 6,564,079 B1 | 5/2003 | Cory |

(56) References Cited

U.S. PATENT DOCUMENTS

| | | |
|---|---|---|
| 6,577,893 B1 | 6/2003 | Besson et al. |
| 6,579,231 B1 | 6/2003 | Phipps |
| 6,605,038 B1 | 8/2003 | Teller et al. |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,800,060 B2 | 10/2004 | Marshall |
| 6,801,137 B2 | 10/2004 | Eggers et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,856,832 B1 | 2/2005 | Matsumura et al. |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,956,917 B2 | 10/2005 | Lenosky |
| 6,957,107 B2 | 10/2005 | Rogers et al. |
| 6,959,929 B2 | 11/2005 | Pugnet et al. |
| 6,961,601 B2 | 11/2005 | Matthews et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,046,649 B2 | 5/2006 | Awater et al. |
| 7,076,437 B1 | 7/2006 | Levy |
| 7,116,252 B2 | 10/2006 | Teraguchi |
| 7,118,531 B2 | 10/2006 | Krill |
| 7,127,300 B2 | 10/2006 | Mazar et al. |
| 7,139,332 B2 | 11/2006 | Yu et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,154,916 B2 | 12/2006 | Soloff |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,105 B2 | 7/2008 | Schmidt et al. |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,505,795 B1 | 3/2009 | Lim et al. |
| 7,510,121 B2 | 3/2009 | Koenck |
| 7,512,448 B2 | 3/2009 | Malick |
| 7,515,043 B2 | 4/2009 | Welch |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,599,003 B2 | 10/2009 | Suzuki et al. |
| 7,616,111 B2 | 11/2009 | Covannon |
| 7,616,710 B2 | 11/2009 | Kim et al. |
| 7,617,001 B2 | 11/2009 | Penner et al. |
| 7,626,387 B2 | 12/2009 | Adachi |
| 7,640,802 B2 | 1/2010 | King et al. |
| 7,647,112 B2 | 1/2010 | Tracey |
| 7,647,185 B2 | 1/2010 | Tarassenko et al. |

(56) References Cited

U.S. PATENT DOCUMENTS

| | | |
|---|---|---|
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,688,204 B2 | 3/2010 | Yamanaka et al. |
| 7,689,437 B1 | 3/2010 | Teller et al. |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,782,991 B2 | 8/2010 | Sobchak et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,904,133 B2 | 3/2011 | Gehman et al. |
| D639,437 S | 6/2011 | Bishay et al. |
| 7,983,189 B2 | 7/2011 | Bugenhagen |
| 8,036,748 B2 | 10/2011 | Zdeblick et al. |
| 8,073,707 B2 | 12/2011 | Teller et al. |
| 8,083,128 B2 | 12/2011 | Dembo et al. |
| 8,114,021 B2 | 2/2012 | Robertson et al. |
| 8,123,576 B2 | 2/2012 | Kim |
| 8,140,143 B2 | 3/2012 | Picard et al. |
| 8,170,515 B2 | 5/2012 | Le Reverend et al. |
| 8,180,425 B2 | 5/2012 | Selvitelli et al. |
| 8,184,854 B2 | 5/2012 | Bartsch |
| 8,193,821 B2 | 6/2012 | Mueller |
| 8,200,320 B2 | 6/2012 | Kovacs |
| 8,214,007 B2 | 7/2012 | Baker et al. |
| 8,238,998 B2 | 8/2012 | Park |
| 8,249,686 B2 | 8/2012 | Libbus et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,332,009 B2 | 12/2012 | McLaughlin et al. |
| 8,360,976 B2 | 1/2013 | Imran |
| 8,369,936 B2 | 2/2013 | Farringdon et al. |
| 8,386,009 B2 | 2/2013 | Lindberg et al. |
| 8,404,275 B2 | 3/2013 | Habboushe |
| 8,440,274 B2 | 5/2013 | Wang |
| 8,471,960 B2 | 6/2013 | Lin et al. |
| 8,514,979 B2 | 8/2013 | Laporte |
| 8,604,974 B2 | 12/2013 | Ganeshan et al. |
| 8,615,290 B2 | 12/2013 | Lin et al. |
| 8,620,402 B2 | 12/2013 | Parker, III et al. |
| 8,754,799 B2 | 6/2014 | Coln et al. |
| 8,773,258 B2 | 7/2014 | Vosch et al. |
| 8,836,513 B2 | 9/2014 | Hafezi et al. |
| 8,932,221 B2 | 1/2015 | Colliou et al. |
| 8,945,005 B2 | 2/2015 | Hafezi et al. |
| 9,014,779 B2 | 4/2015 | Zdeblick et al. |
| 9,149,577 B2 | 10/2015 | Robertson et al. |
| 9,158,890 B2 | 10/2015 | Meredith et al. |
| 2001/0027331 A1 | 10/2001 | Thompson |
| 2001/0031071 A1 | 10/2001 | Nichols et al. |
| 2001/0044588 A1 | 11/2001 | Mault |
| 2001/0051766 A1 | 12/2001 | Gazdinski |
| 2001/0056262 A1 | 12/2001 | Cabiri et al. |
| 2002/0002326 A1 | 1/2002 | Causey et al. |
| 2002/0026111 A1 | 2/2002 | Ackerman |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0169696 A1* | 11/2002 | Zara .................. G06Q 10/06 705/28 |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0091121 A1 | 5/2003 | Kenmochi |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0229382 A1 | 12/2003 | Sun et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0010338 A1 | 1/2005 | Kraeling et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |

(56) References Cited

U.S. PATENT DOCUMENTS

| | | |
|---|---|---|
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0136744 A1 | 6/2006 | Lange |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0255064 A1 | 11/2006 | Donaldson |
| 2006/0265246 A1 | 11/2006 | Hoag |
| 2006/0270346 A1 | 11/2006 | Ibrahim |
| 2006/0277097 A1 | 12/2006 | Shafron et al. |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0014866 A1 | 1/2008 | Lipowshi |
| 2008/0015421 A1 | 1/2008 | Penner |
| 2008/0015494 A1 | 1/2008 | Santini et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0045843 A1 | 2/2008 | Tsuji et al. |
| 2008/0046038 A1 | 2/2008 | Hill |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0139907 A1 | 6/2008 | Rao et al. |
| 2008/0139953 A1* | 6/2008 | Baker ............... A61B 5/0006 600/509 |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0183245 A1 | 7/2008 | Van Oort |
| 2008/0188837 A1 | 8/2008 | Belsky et al. |
| 2008/0194912 A1 | 8/2008 | Trovato et al. |

(56) References Cited

U.S. PATENT DOCUMENTS

| | | |
|---|---|---|
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0088618 A1 | 4/2009 | Ameson |
| 2009/0099435 A1 | 4/2009 | Say et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0010330 A1 | 1/2010 | Rankers |
| 2010/0033324 A1 | 2/2010 | Shimizu et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0049263 A1 | 2/2010 | Reeve |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |

(56) References Cited

U.S. PATENT DOCUMENTS

| | | |
|---|---|---|
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0298650 A1 | 11/2010 | Moon et al. |
| 2010/0298730 A1 | 11/2010 | Tarassenko et al. |
| 2010/0311482 A1 | 12/2010 | Lange |
| 2010/0312580 A1 | 12/2010 | Tarassenko et al. |
| 2011/0004079 A1 | 1/2011 | Al-Ali et al. |
| 2011/0040203 A1 | 2/2011 | Savage et al. |
| 2011/0065983 A1 | 3/2011 | Hafezi et al. |
| 2011/0081860 A1 | 4/2011 | Brown et al. |
| 2011/0124983 A1 | 5/2011 | Kroll et al. |
| 2011/0144470 A1 | 6/2011 | Mazar et al. |
| 2011/0166937 A1 | 7/2011 | Bangera et al. |
| 2011/0237924 A1 | 9/2011 | McGusty et al. |
| 2011/0279963 A1 | 11/2011 | Kumar et al. |
| 2012/0016231 A1 | 1/2012 | Westmoreland |
| 2012/0029307 A1 | 2/2012 | Paquet et al. |
| 2012/0029309 A1 | 2/2012 | Paquet et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0197144 A1 | 8/2012 | Christ et al. |
| 2012/0299723 A1 | 11/2012 | Hafezi et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2014/0300490 A1 | 10/2014 | Kotz et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0131764 A1 | 5/2015 | Kushner et al. |
| 2015/0182170 A1 | 7/2015 | Zdeblick et al. |
| 2015/0248833 A1 | 9/2015 | Arne et al. |

FOREIGN PATENT DOCUMENTS

| | | |
|---|---|---|
| CN | 101005470 | 7/2007 |
| CN | 101032396 | 9/2007 |
| CN | 201076456 | 6/2008 |
| DE | 10313005 | 10/2004 |
| EP | 1246356 | 10/2002 |
| EP | 1789128 | 5/2007 |
| EP | 2063535 | 5/2009 |
| EP | 2143369 | 1/2010 |
| JP | 61072712 | 4/1986 |
| JP | S62112529 | 5/1987 |
| JP | 05-228128 | 9/1993 |
| JP | 10-14898 | 1/1998 |
| JP | 2000-506410 | 5/2000 |
| JP | 2002-224053 | 8/2002 |
| JP | 2002282219 | 10/2002 |
| JP | 2002291684 | 10/2002 |
| JP | 2004-7187 | 1/2004 |
| JP | 2004313242 | 11/2004 |
| JP | 2005-073886 | 3/2005 |
| JP | 2005-304880 | 4/2005 |
| JP | 2005137683 | 6/2005 |
| JP | 2005-532841 | 11/2005 |
| JP | 2005-532849 | 11/2005 |
| JP | 2006508752 | 3/2006 |
| JP | 2006509574 | 3/2006 |
| JP | 2006136405 | 6/2006 |
| JP | 2006-177699 | 7/2006 |
| JP | 2007167448 | 7/2007 |
| JP | 2007-313340 | 12/2007 |
| JP | 2008011865 | 1/2008 |
| JP | 2008501415 | 1/2008 |
| JP | 2008086390 | 4/2008 |
| JP | 2008191110 | 8/2008 |
| KR | 927471 | 11/2009 |
| KR | 10-2012-09995 | 9/2012 |
| TW | 553735 | 9/2003 |
| TW | 200724094 | 7/2007 |
| WO | WO8802237 | 4/1988 |
| WO | WO9308734 | 5/1993 |
| WO | WO9319667 | 10/1993 |
| WO | WO9714112 | 4/1997 |
| WO | WO9843537 | 10/1998 |
| WO | WO9959465 | 11/1999 |
| WO | WO0033246 | 6/2000 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO2004014225 | 2/2004 |
| WO | WO2004039256 | 5/2004 |
| WO | WO2004059551 | 7/2004 |
| WO | WO2004066834 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | WO2005013503 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005055448 | 6/2005 |
| WO | WO2005082436 | 9/2005 |
| WO | WO2005110238 | 11/2005 |
| WO | WO2006027586 | 3/2006 |
| WO | WO2006035351 | 4/2006 |
| WO | WO2006046648 | 5/2006 |
| WO | WO2006055892 | 5/2006 |
| WO | WO2006055956 | 5/2006 |
| WO | WO2006066566 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |

(56) References Cited

FOREIGN PATENT DOCUMENTS

| WO | WO2007036746 | 4/2007 |
|---|---|---|
| WO | WO2007040878 | 4/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080843 | 7/2010 |
| WO | WO2010105053 | 9/2010 |
| WO | WO2010107563 | 9/2010 |
| WO | WO2010115194 | 10/2010 |
| WO | WO2010135516 | 11/2010 |
| WO | WO2012104657 | 8/2012 |
| WO | WO2012158190 | 11/2012 |
| WO | WO2013012869 | 1/2013 |
| WO | WO2015042411 | 3/2015 |
| WO | WO2015044722 | 4/2015 |
| WO | WO2015112603 | 7/2015 |

OTHER PUBLICATIONS

Arshak et al., A Review and Adaptation of Methods of Object Tracking to Telemetry Capsules IC-Med (2007) vol. 1, No. 1, Issue 1, 12 pp.
"ASGE Technology Status Evaluation Report: wireless capsule endoscopy" American Soc. for Gastrointestinal Endoscopy (2006) vol. 63, No. 4; 7 pp.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Carlson et al., "Evaluation of a non-invasive respiratory monitoring system for sleeping subjects" Physiological Measurement (1999) 20(1): 53.
Delvaux et al., "Capsule endoscopy: Technique and indications" Clinical Gastoenterology (2008) vol. 22, Issue 5, pp. 813-837.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12: 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Heydari et al., "Analysis of the PLL jitter due to power/ground and substrate noise"; IEEE Transactions on Circuits and Systems (2004) 51(12): 2404-16.
Hoover et al., "Rx for health: Engineers design pill that signals it has been swallowed" University of Florida News (2010) 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
ISFET—Ion Sensitive Field-Effect Transistor; Microsens S.A. pdf document. First cited by Examiner in Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
MacKay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Medtronic, "CareLink Therapy Management Software for Diabetes" (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® Real-Time Revel™ System" (2010) http://www.medtronicdiabetes.com/products/index.html; 2 pp.
Medtronic, "Mini Med Paradigm ® Revel™ Insulin Pump" (2010) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Mini Mitter Co, Inc. 510(k) Premarket Notification Mini-Logger for Diagnostic Spirometer. Sep. 21, 1999.
Mojaverian et al., "Estimation of gastric residence time of the Heidelberg capsule in humans: effect of varying food composition" Gastroenterology (1985) 89:(2): 392-7.
NPL_AntennaBasics.pdf, Radio Antennae, http://www.erikdeman.de/html/sail018h.htm; (2008) 3pp.
Park, "Medtronic to Buy MiniMed for $3.7 Billion" (2001) HomeCare; http://homecaremag.com/mag/medical_medtronic_buy_minimed/; 2 pp.

(56) References Cited

OTHER PUBLICATIONS

Sanduleanu et al., "Octave tunable, highly linear, RC-ring oscillator with differential fine-course tuning, quadrature outputs and amplitude control for fiber optic transceivers" (2002), IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6 (2002), p. 329-334.
"Smartlife awarded patent for knitted transducer" Innovation in Textiles News: http://www.innovationintextiles.com/articles/208.php; 2pp. (2009).
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Walkey, "MOSFET Structure and Processing"; 97.398* Physical Electronics Lecture 20; First cited by Examiner in Office Action dated Jun. 13, 2011 for U.S. Appl. No. 12/238,345; 24 pp.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
Evanczuk, S., "PIC MCU software library uses human body for secure communications link" EDN Network; edn.com; Feb. 26, 2013 Retrieved from internet Jun. 19, 2013 at http://www.edn.com/electronics-products/other/4407842/PIC-MCU-software-library-uses-human-body-for-secure-communications-link; 5 pp.

* cited by examiner

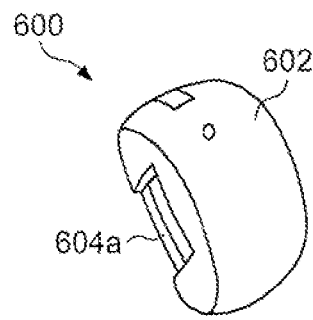
FIG. 6
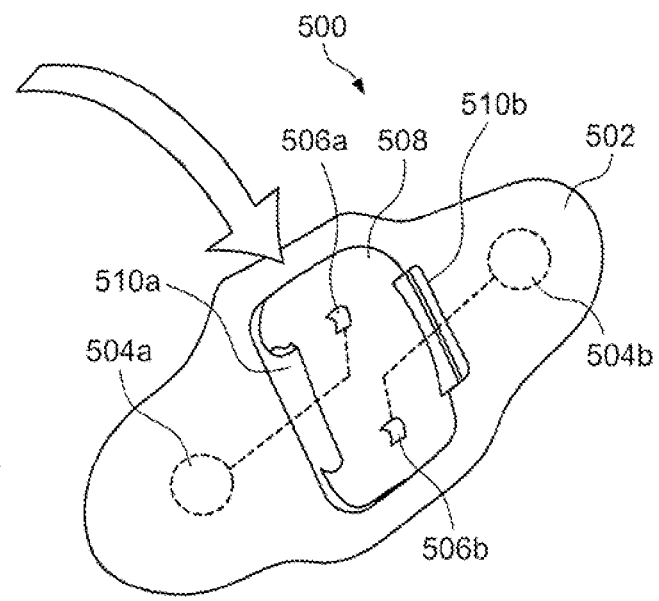
FIG. 5
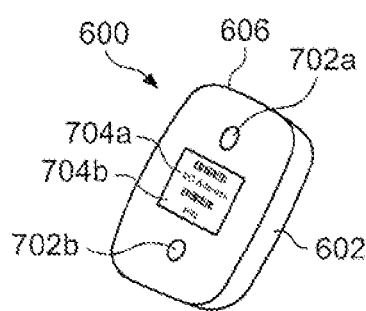
FIG. 7
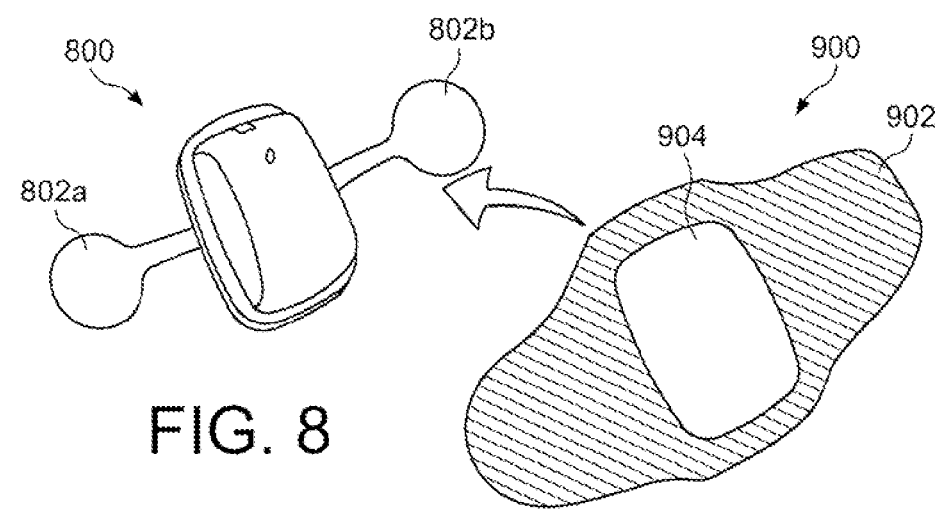
FIG. 8
FIG. 9

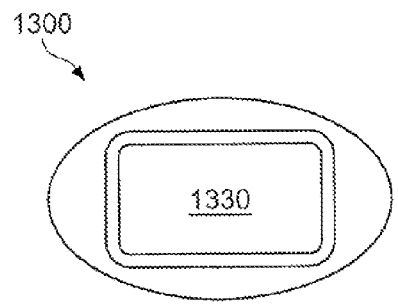 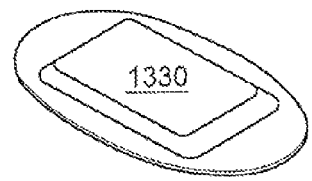
FIG. 16A  FIG. 16B
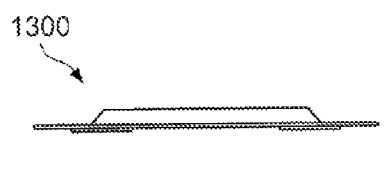 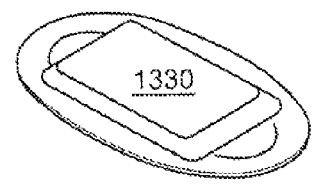
FIG. 16C
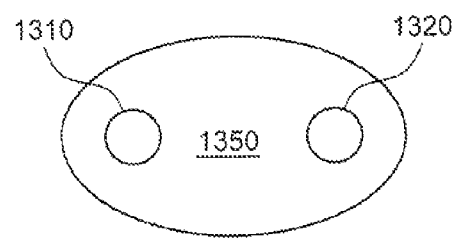 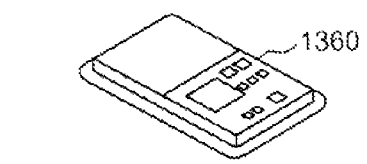
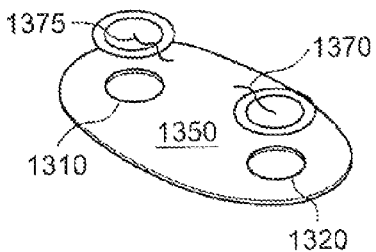
FIG. 16D  FIG. 16E

RE-WEARABLE WIRELESS DEVICE

CROSS-REFERENCE TO RELATED APPLICATIONS

Introduction

The present disclosure is related generally to a re-wearable wireless device. More particularly, the present disclosure is related to a re-wearable wireless device configured to monitor at least one parameter and to wirelessly communicate the at least one monitored parameter to a communication network. The communication network communicates the at least one monitored parameter to a remote device, such as a back end server, over the communication network or other wide area network. The at least one monitored parameter may include, without limitation, skin impedance, electro cardiogram signals, conductively transmitted current signal, position of wearer, temperature, heart rate, perspiration rate, humidity, altitude/pressure, global positioning system (GPS), proximity, bacteria levels, glucose level, chemical markers, blood oxygen levels, among other physiological and physical parameters.

Current wearable wireless device architectures communicate to a hub, basestation, telephone using low power wireless protocols such as Bluetooth, Bluetooth low energy (BLE) ZigBee, ANT, proprietary, and the like, which then passes the data collected onto remote servers via wired connection, plain old telephone service (POTS), cellular data, etc. New mobile chipsets permit the incorporation of a cellular data modem/phone into a personal wireless wearable thereby simplifying the overall system design/improving usability while reducing the cost of the service.

Additional issues concerning current wearable wireless devices include high cost to manufacturer electronics portion, user discomfort associated with extended wear of the adhesive portions or portions that come in contact with the skin, etc.

SUMMARY

In one aspect, a re-wearable wireless device is provided. The re-wearable wireless device comprises a reusable component configured to be secured to a disposable component. The reusable component comprises a sensor interface configured to receive signals from at least one electrode configured to be secured to a living subject and monitors one or more physiological and physical parameters associated with the living subject and a cellular wireless communication circuit.

In another aspect, an adhesive base for a re-wearable wireless device is provided. The re-wearable adhesive base comprises a first adhesive layer and a second adhesive layer partially covering the first adhesive layer around a perimeter of the first adhesive layer. The first adhesive layer includes a first adhesive and the second adhesive layer comprises a second adhesive.

In yet another aspect, a method of establishing a link between two wireless devices is provided. According to the method, a first wireless device is provided with an insignia representing a communication channel address identification. An image of the insignia is captured with a mobile telephone computing device comprising an image sensor. The captured image is processed to extract the communication channel address identification represented by the insignia.

Still in other aspects, a re-wearable wireless device in accordance with the present disclosure comprises a reusable component and a disposable component. The reusable component may comprise a mobile chipset, energy source, sensors, and the like. The disposable component may comprise electrodes and/or adhesive for adhering the disposable component the skin of a living subject, be it human or animal. The disposable component may comprise at least two-forms of adhesive.

FIGURES

FIG. 5 illustrates one aspect of a disposable component comprising an adhesive base, electrodes (shown in phantom), electrical contacts, and a mechanical snap-in connect mechanism.

FIG. 6 is a perspective top view of one aspect a reusable component comprising an electronics module located within a housing configured to mate with the mechanical snap-in connect mechanism of the disposable component shown in FIG. 5.

FIG. 7 is a perspective bottom view of one aspect of a reusable component.

FIG. 8 illustrates one aspect of a reusable component.

FIG. 9 illustrates one aspect of an adhesive overlay.

Figure 12A:
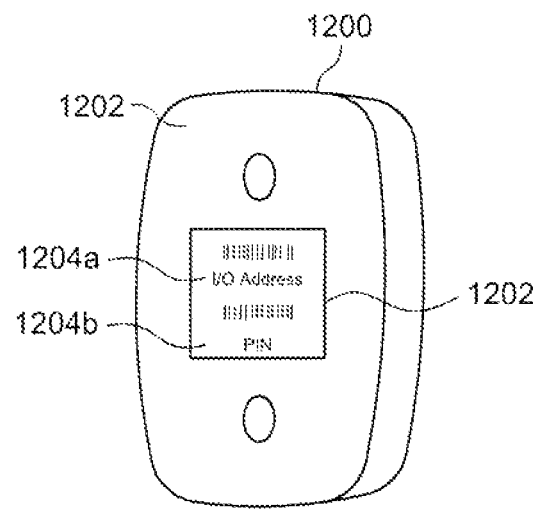

FIGS. 12A and B illustrate one aspect of a process of capturing an image of the Input/Output (I/O) Address and personal identification number (PIN) located on a bottom portion of a reusable component.

Figure 13:
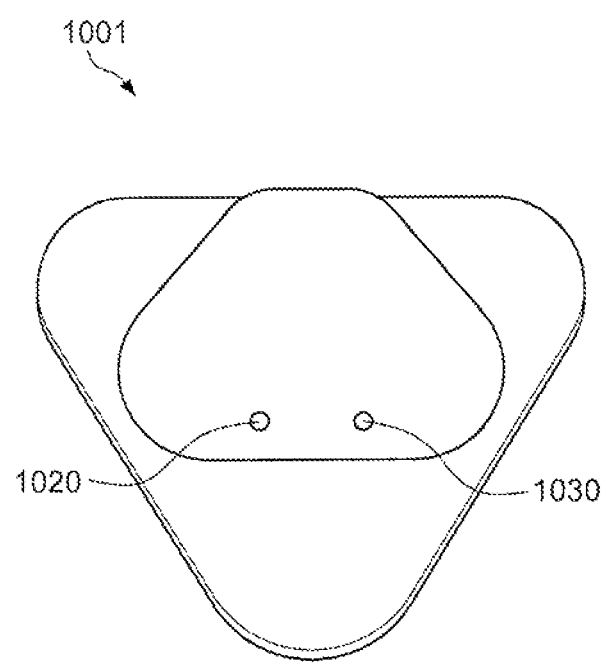

FIG. 13 is a three-dimensional view of an external signal receiver, according to one aspect.

Figure 10:
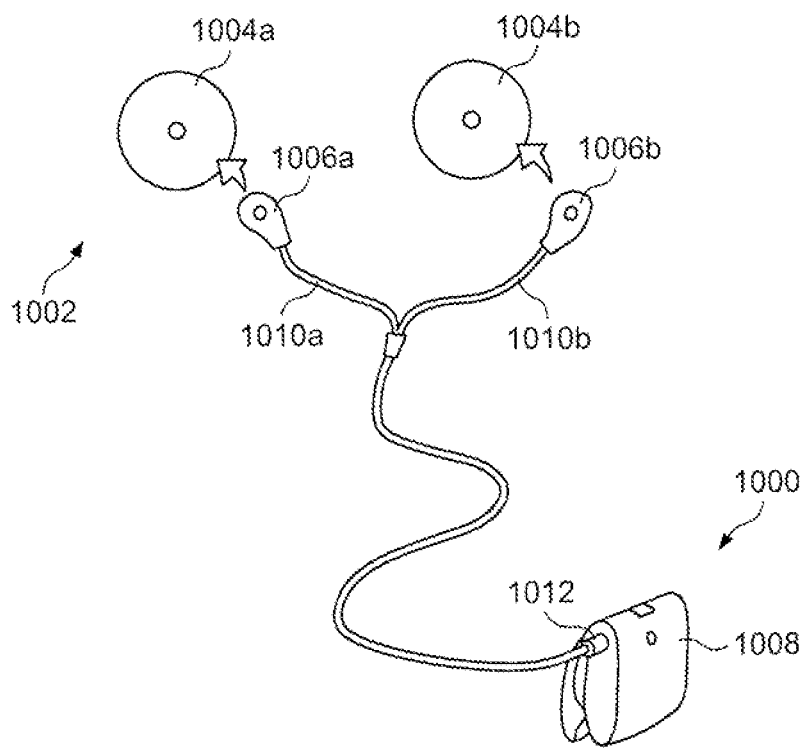
FIG. 10 illustrates one aspect of a re-wearable wireless device comprising a reusable component and a disposable component.
Figure 14:
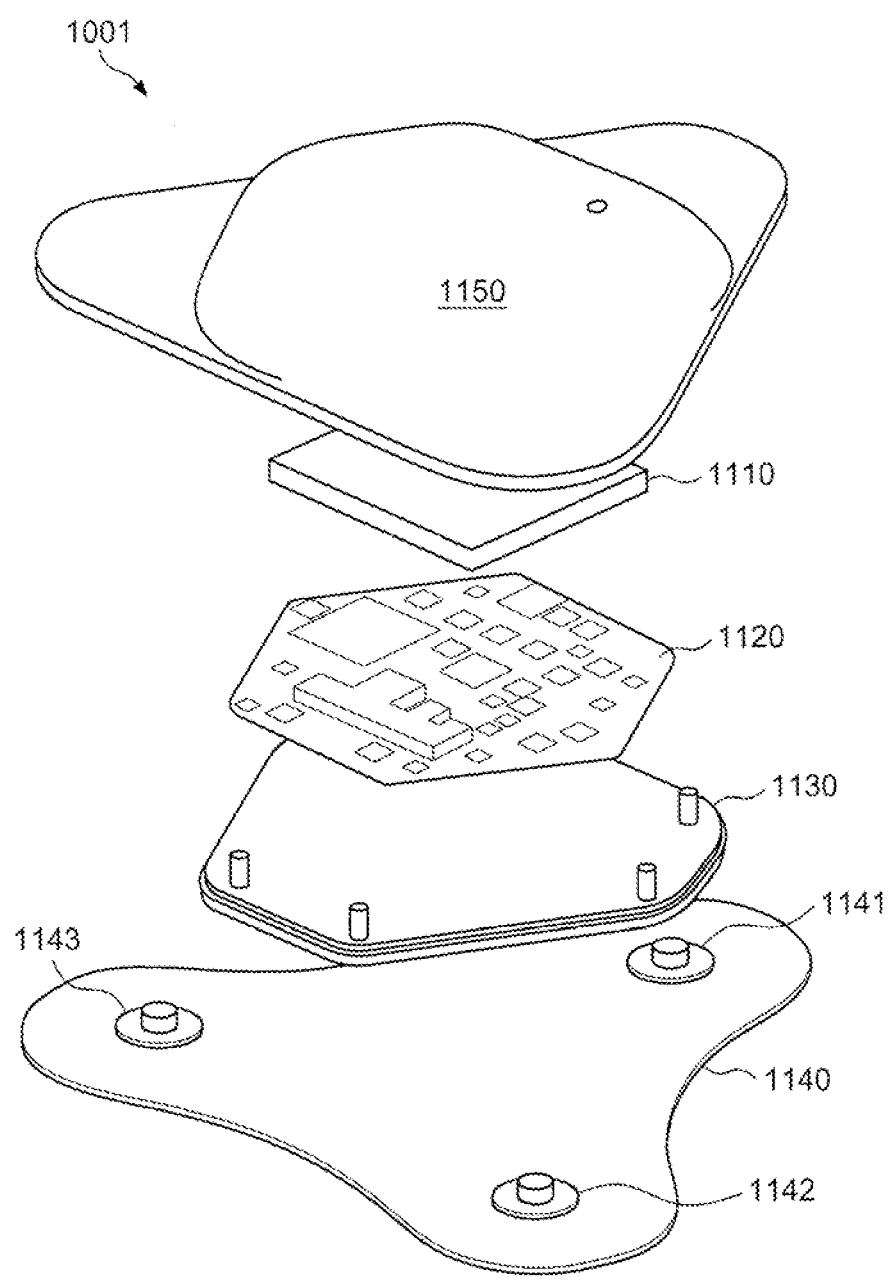

FIG. 14 provides an exploded view of the signal receiver shown in FIG. 10, according to one aspect.

Figure 15:
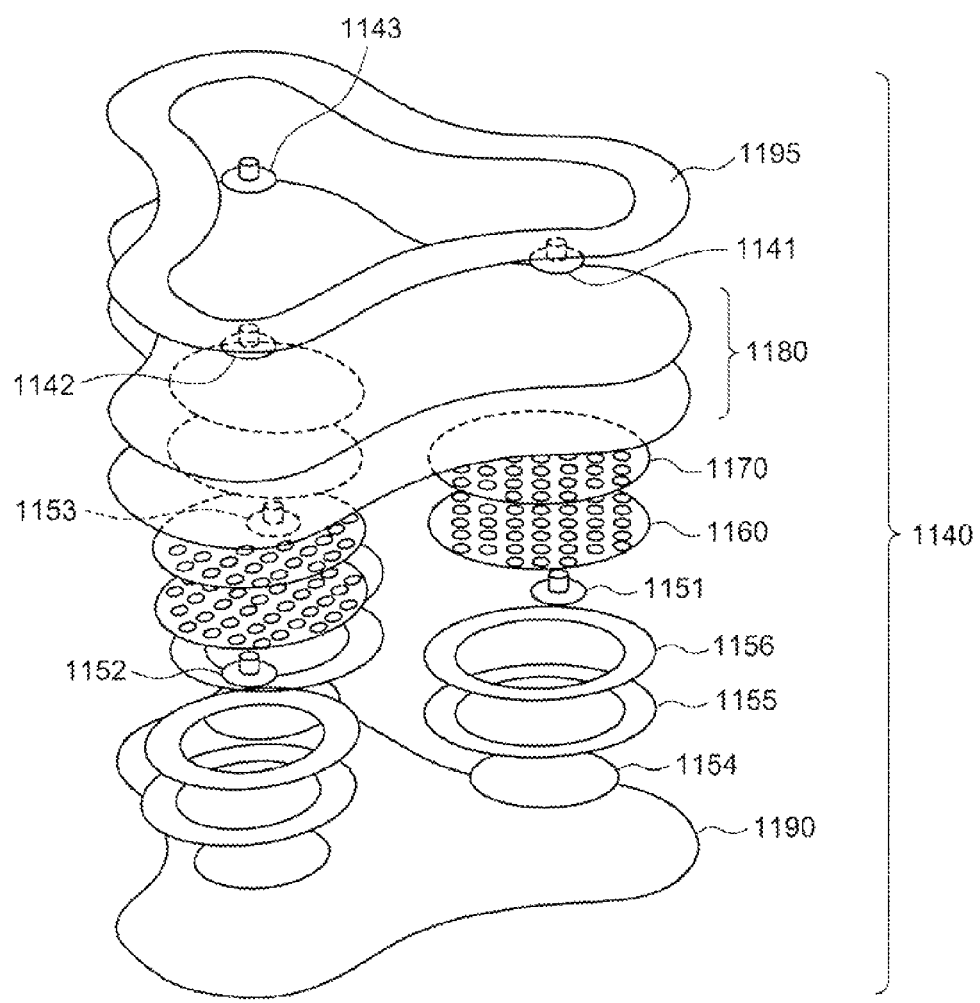

FIG. 15 provides an exploded view of the adhesive patch component of the signal receiver shown in FIGS. 13 and 14, according to one aspect.

FIGS. 16A to 16E provide various views of a two-electrode external signal receiver, according to one aspect.

DESCRIPTION

Before explaining the various embodiments of the wireless wearable apparatus, system, and method in detail, it should be noted that the various embodiments disclosed herein are not limited in their application or use to the details of construction and arrangement of parts illustrated in the accompanying drawings and description. Rather, the disclosed embodiments are may be positioned or incorporated in other embodiments, variations and modifications thereof, and may be practiced or carried out in various ways. Accordingly, embodiments of the wireless wearable apparatus, system, and method disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

In the following description, like reference characters designate like or corresponding parts throughout the several views. Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

The present disclosure is directed generally to various aspects of a wireless wearable apparatus, system, and method for monitoring at least one physiological and/or physical parameter associated with the wearer of the re-wearable wireless device and for communicating the monitored parameter to a communication device. The communication device is configured to communicate the monitored parameter remotely over a network.

It will be appreciated that the term "medication" or "dose form" as used throughout this disclosure includes various forms of ingestible, inhalable, injectable, absorbable, or otherwise consumable medicaments and/or carriers therefor such as, for example, pills, capsules, gel caps, placebos, over capsulation carriers or vehicles, herbal, over-the-counter (OTC) substances, supplements, prescription-only medication, ingestible event markers (IEM), and the like.

Figure 1:
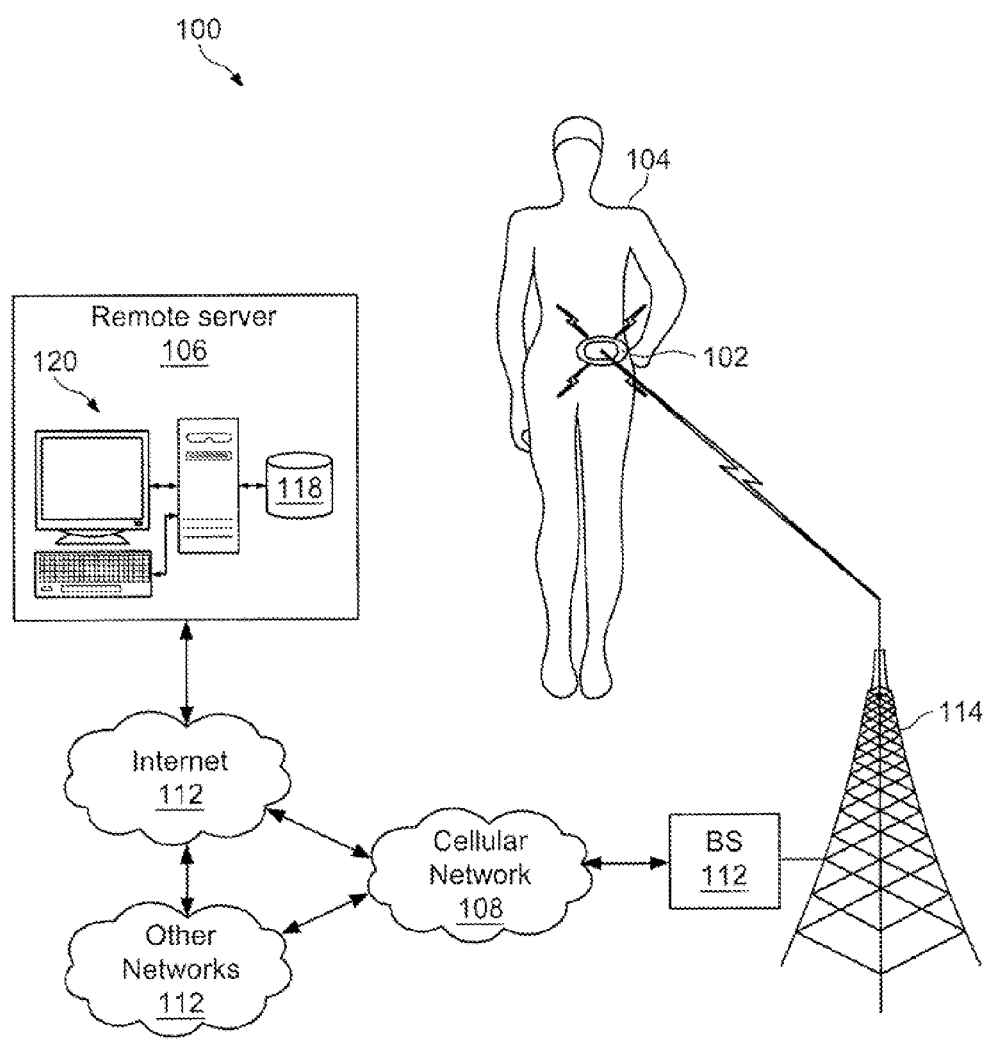
FIG. 1 illustrates one aspect of a wireless communication system comprising a re-wearable wireless device with a mobile chipset.

FIG. 1 illustrates one aspect of a wireless system 100 comprising a re-wearable wireless device 102 comprising a mobile chipset, e.g., single- or multi-chip cellular radio modem. In one aspect, the re-wearable wireless device 102 is removably attachable to a living subject 104, such as a person or other biological life form. In one aspect, the re-wearable wireless device 102 is configured to monitor at least one parameter. The at least one monitored parameter may include, for example, a physiological and/or physical parameter associated with the subject. For example, the re-wearable wireless device 102 may be configured to monitor parameters, such as, without limitation, skin impedance, electro cardiogram signals, conductively transmitted current signal, position of wearer, temperature, heart rate, perspiration rate, humidity, altitude/pressure, global positioning system (GPS), proximity, bacteria levels, glucose level, chemical markers, blood oxygen levels, among other physiological and physical parameters.

In one aspect, the mobile phone is configured to wirelessly communicate the at least one monitored parameter over a communication network to a back-end or remote server or remote node 106 over the communication network. In one aspect, the communication network is a cellular network or a cellular communication network 108. The mobile chipset enables the re-wearable wireless device 102 to make and receive data over a radio link while moving around a wide geographic area. It does so by connecting to the cellular communication network 108 provided by a mobile phone operator and allowing access to the public telephone network. The communication network communicates with other networks 110 or the Internet 112 to access the back-end server 106. The amount of data transmitted by re-wearable wireless device 102 may be about 10 kilobytes per day to about 100-150 kilobytes per day, for example.

In one aspect, when the re-wearable wireless device 102 is activated and initiates a wireless transmission of information associated with the monitored parameter(s) using the mobile chipset. The information associated with the monitored parameter(s) may include, for example, raw measurement data, processed data, and/or any combination thereof. The information also may include an identification number, patient identification information (e.g., name, address, phone number, email, social network web address), dosing unit identification, ingestible event marker system identification, time and date stamp when a dose form package is opened, time and date stamp when the ingestible event marker system was ingested by the patient and activated, among other information.

When the re-wearable wireless device 102 is activated the re-wearable wireless device 102 communicates with a cell tower 114 and base station (BS) 116 and can access the Internet 112 via the cellular communication network 108. Accordingly, information received by the re-wearable wireless device 102 from the subject 104 can be communicated to the remote node 106 via the Internet 112 or other networks 110. A processing system 120 at the remote node 106 receives the information and stores it for processing by the database 118.

Still with reference to FIG. 1, the remote node 106 comprises a processing system 120 communicatively coupled to a database 118. Information associated with all subjects 104, e.g., patients, including identity and medication types and doses, may be stored in the database 118. The processing system 120 receives information from the re-wearable wireless device 102 and accesses the information in the database 118 associated with the remote node 106 to provide information to the care provider through the re-wearable wireless device 102. The remote node 106 can communicate information including a photo of the patient for identification, the type of medication available to the care provider, as well as confirmation of the type and dose of medication that the care provider selects and delivers to the patient. The re-wearable wireless device 102 can communicate with the remote node 106 using any mode and frequency of communication that is available in at the site, such as wireless, G2, G3, G4, real-time, periodically based on predetermined time delays, as well as store and forward at later time.

Vehicles of communication between the re-wearable wireless device 102 and the remote node 106 include one or more networks. In various aspects, the network comprises local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

The processing system 120 at the remote node 106 may comprise servers configured as desired, e.g., to provide for subject directed permissions. For example, the servers may be configured to allow a family caregiver to participate in the subject's therapeutic regimen, e.g., via an interface (such as a web interface) that allows the family caregiver to monitor alerts and trends generated by the server, and provide support back to the patient. The servers also may be configured to provide responses directly to the subject, e.g., in the form of subject alerts, subject incentives, which are relayed to the subject via the communication device. The servers also may interact with a health care professional, e.g., RN, physician, which can use data processing algorithms to obtain measures of health and compliance of the subject, e.g., wellness index summaries, alerts, cross-patient benchmarks, and provide informed clinical communication and support back to the patient. The servers also may interact with pharmacies, nutrition centers, and drug manufactures.

In one aspect, the remote node 106 may store in the database 118 the time and date when a dose form was taken by the subject 104. In addition, when an event marker system is provided in the dosing unit, the time and date stamp of when the event marker system was ingested by the patient also may be stored in the database 118. In addition, an identification number such as a serial number, for example, identifying the single- or multi-dose packages, the type of package (single, multiple, morning, afternoon, evening, daily, weekly, monthly dosing event, and so on) the individual patient identification, the date of pre-packaging, the source, and the contents of the package, for example, may be stored in the database 118. In some aspects, the expiration date or shelf life of one or all of the medication(s) or dose forms also may be stored in the database 118.

The mobile chipset in the re-wearable wireless device 102 provides two-way data communication between the re-wearable wireless device 102 and the cellular communication network 108 via the cell tower 114. In one aspect, when the subject 104 ingests a dose form comprising an event indicator system, the event indicator system communicates with the re-wearable wireless device 102, which includes various electronic modules for receiving a unique signature from the event indicator system and communicating with the cellular communication network 108. It will be appreciated, that in various aspects, the re-wearable wireless device 102 may be configured to communicate with an access point as well as other mobile device(s). Thus the re-wearable wireless device 102 can effectively communicate with the remote node 106 via the Internet 112 through a local area network (LAN) or the cellular communication network 114.

In other aspects, the re-wearable wireless device 102 can be triggered to initiate a data transmission to the cellular communication network 108 based on a variety of triggers. These triggers include, without limitation, a timer, real time clock, an event, detection of ingestion of an event marker system, detection of a particular code received from the event marker system, receipt of a particular monitored parameter or value of such monitored parameter, receipt of trigger data from the cellular communication network 108, among others.

Figure 2:
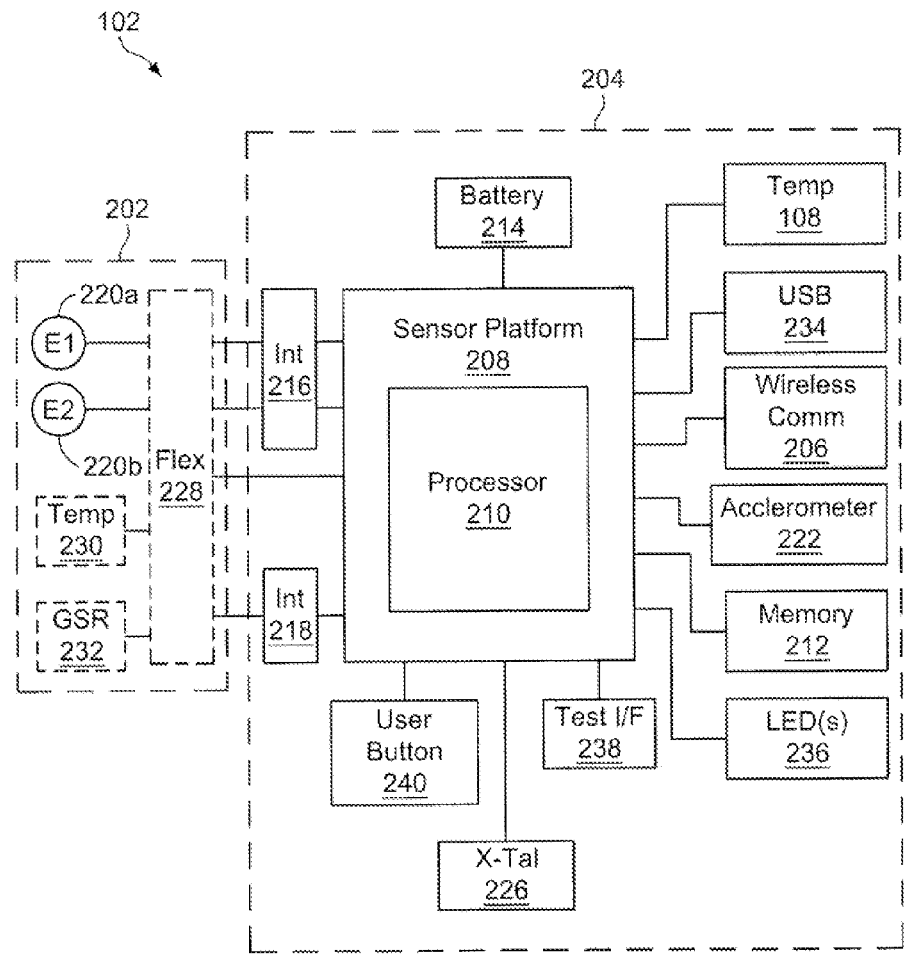
FIG. 2 is a system diagram of one aspect of the re-wearable wireless device.

FIG. 2 is a system diagram of one aspect of the re-wearable wireless device 102. In one aspect, the re-wearable wireless device 100 is a two-piece device comprising a disposable component 202 and a reusable component 204. The reusable component 204 comprises an electronics module. The electronics module of the reusable component 204 comprises a wireless communication circuit 206, such as a mobile chipset RF wireless circuit or simply cellular radio. The electronics module of the reusable component 204 comprises an ASIC-based sensor platform 208 that includes a hardware architecture and software framework to implement various aspects of the re-wearable wireless device 102. In one aspect, the ASIC-based sensor platform 208 may be disposed on and interfaced with a printed circuit board assembly (PCBA). The wireless communication circuit 206 may be a low power mobile chipset and is configured to connect to the cellular network 108 as well as other wireless devices (cell-phones, smart phones, tablet computers, laptop computers, gateway devices, among others). The disposable component 202 interfaces with the PCBA and the first electronic module 204. In one aspect, the electronic module 204 and the disposable component 202, each may comprises additional modules that reside on or off the PCBA or, in another aspect may be disposed on the PCBA.

In one aspect, the reusable electronic module 204 provides a sensor platform and comprises circuits designed to interface with different sensors and comprises various combinations of the following components. In various aspects, the reusable electronic module 204 ASIC-based sensor platform provides a combination of analog front-end, vector/digital signal processing, microprocessor and memory in a single low-power ASIC/chip that comprises an "ASIC-based sensor platform" 208 with multiple functions: software-defined radio for detection of ingestible event markers, sensing and decoding of ECG, AC skin impedance measurements, temperature measurements, DC skin impedance (e.g., GSR) measurements and other biological/medical data sensors.

In one aspect, the reusable electronic module 204 comprises an ASIC sensor platform 208, a controller or processor 210, e.g., a microcontroller unit (MCU), a radio frequency (RF) wireless comm circuit 206, among other components described hereinbelow.

In one aspect, the ASIC portion 208 of the reusable electronic module 204 may comprise a core processor 210 such as, for example, an ARM Cortex™ M3 processor, for real-time applications, a signal processing accelerator such as, for example, a Vector Math Accelerator, program memory, data memory, serial interfaces such as, for example, SPI, universal asynchronous receiver transmitter (UART), two-wire multi-master serial single ended bus interface (I2C), general purpose input/output (GPIO), a real-time clock, an analog-to-digital converter (ADC), gain and conditioning circuits for bio-potential signals, light emitting diode (LED) drivers, among other components. The reusable electronic module 204 also comprises a connection port to external memory, a connection port to external sensors, and a hardware accelerator. The processor 210 receives a signal from each of the sensors by operating the analog front end for analog sensors and by receiving digital data from sensors with the ADC digitizer. The processor 210 then processes the data and stores the results into the memory 212 in form of data records. In one aspect, the processor 210 may have a very long instruction word (VLIW) processor architecture.

In one aspect, the reusable electronic module 204 also comprises a universal serial bus 234 (USB), an accelerometer 222, memory 212, one or more LEDs 236, test interface 238 (I/F), a 32 KHz crystal 226, a user button 240 that may be used to initiate a communication connection with an external device, sensor interfaces 216, 218, and a battery 214 (e.g., coin cell, primary battery cell). In one aspect, the battery 214 may a rechargeable cell rather than a primary battery cell. In other aspects, the reusable electronic module 204 may comprise a gyroscope, and circuits for processing ECG, temperature, and accelerometer signals. In other aspects, the reusable electronic module 204 also may comprise body composition and $SpO_2$ pulse oximetry circuits that monitor functional oxygen saturation of arterial blood by calculating the ratio of oxygenated hemoglobin to hemoglobin that is capable of transporting oxygen. An SpO2 pulse oximetry circuit may be configured to provide continuous, noninvasive measurements of SpO2 and, in one aspect, can display a plethysmographic waveform. Heart rate values are may be derived from the pulse oximetry signal.

In one aspect, the reusable electronic module 204 comprises an RF wireless communication circuit 206. The RF wireless communication circuit 206 comprises an antenna for receive and transmit wireless signals, a transmitter circuit, a receiver circuit, and a link master controller that includes a mechanism to connect (establish a link) to another, external, wireless device and transfer data, as described in more detail hereinbelow. In one aspect, the link master controller establishes connection to an external device. As a master of the link, the link master controller performs control of data transmission over the link to the external device, including timing control and radio frequency control (channel hopping). The link master controller sends a signal to the external device with an instruction that gives number of data records stored in memory (a total number of all data records and a total number of records of each data type). In various aspects, the RF wireless communication circuit 206 may be implemented using a mobile chipset available from a variety of vendors including, without limitation Tegra by Nvidia, Snapdragon by Qualcomm, OMAP by Texas Instruments, Exynos by Samsung, Ax by Apple, NovaThor by ST-Ericsson, Atom by Intel, i.MX by Freescale Semiconductor, RK3xxx by Rockchip, A31 by AllWinner, among others. Such mobile chipsets are employed by mobile telephones, otherwise known in the art as "mobile," "wireless," "cellular phone," "cell phone," "hand phone (HP)," "smart phone," among others.

After each connection, the processor 210 continues to receive all sensor signals, processes the data and stores new data records into the memory 212. Upon each subsequent connection link master controller sends a signal to an external device with new data records since last connection and confirms that records were transmitted successfully. The link master controller receives a signal from the external device that establishes if the external device is ready to receive data records and also receives a signal from the external device that establishes which data records were not transferred successfully. The link master controller avoids repeating the transmission of the data records that already have been transmitted, which improves battery 214 power use for a longer operation and resends all data records that were not transferred successfully. The link master controller may delete from the memory all or some successfully transferred data records at a later time (for example, when the memory 212 gets full).

In one aspect, the reusable electronic module 204 comprises a sensor interfaces 216, 218 between electrodes 220a, 220b (E1, E2) and one or more band pass filters or channels. The sensor interfaces 216, 218 provide an analog front end and may include programmable gain or fixed gain amplifiers, programmable low-pass filter, programmable high-pass filter. The sensor interfaces 216, 218 may comprise active signal conditioning circuits including strain gauge measurement circuits, for example. One channel receives low frequency information associated with the physiological data of the subject (e.g., user) and the other channel receives high frequency information associated with an electronic device within the subject. In one alternative aspect, an additional channel is provided for receiving DC data of the subject. The high frequency information is passed to a digital signal processor (DSP) implemented in the ASIC portion 208 and then to a processor 210 (e.g., a control processor) portion of the re-wearable wireless device 102 for decompression and decoding. The low frequency information is either passed to the DSP portion of the ASIC portion 208 and then to processor 210, or passed directly to the processor 210. The DC information is passed directly to the processor 210. The DSP portion of the ASIC portion 208 and the processor 210 decode the high frequency, low frequency and DC information or data. This information is then processed and prepared for transmission.

In one aspect, signal processing may or may not be applied to the raw data collected. Signal processing may occur in the real space, complex number space, or in the polar coordinates space. Functions include filters, e.g., finite impulse response (FIR) and infinite impulse response (IIR), mixers, fats Fourier transforms (FFTs), cordics, and others. Raw data may simply be stored and processed downstream. The signal processing may occur in the processor (e.g., ARM Cortex™ M3) or may occur in the signal processing accelerator which is incorporated into the ASIC portion 208.

In one aspect, the reusable electronic module 204 comprises an accelerometer 222 and one or more temperature sensors 224. In one aspect, two temperature sensors are provided that are identical but placed in different locations— one close to the skin, another close to the ambient for measuring additional data. The temperature sensors 224 may be configured to measure and record, skin, ambient, and circuit board temperature. The temperature sensors 224 may be used to measure heat flux between the skin and the ambient temperature sensor. In one aspect, the temperature sensor 224 or sensors are thermistor devices with negative temperature coefficient (NTC) or positive temperature coefficient (PTC), and in another aspect temperature sensor 224 or sensors are using integrated semiconductor devices. This information is provided to the processor 210 and can be processed by the processor 210 and prepared for transmission by a transmitter portion of the RF wireless communication circuit 206. The physiological information measured is processed by the processor 210 and may be transmitted as real-time or raw data, or derived quantities or parameters may be transmitted.

In one aspect, the accelerometer 222 may be a 3-axis accelerometer with a resampling frequency correction processor. Digital accelerometer 222 sensors usually include a MEMS-based acceleration sensor element, a digitizer, and digital interface control logic. Typically these accelerometers use resistor-capacitor (RC) oscillator with low accuracy to strobe the digitizer sampling input. In order to employ signals from such accelerometer 222 in signal processing algorithms the accuracy of RC oscillators is not sufficient. Accordingly, in one aspect, the reusable electronic module 204 comprises an accelerometer sampling frequency correction processor that takes signals from the accelerometer 222 and performs re-sampling to compensate for the RC oscillator error.

In one aspect, the accelerometer 222 sampling frequency correction processor comprises a reference clock (high accuracy oscillator), a fixed up-sample block, a digital filter, a programmable down-sample block, and a control circuit that selects down-sample coefficient based on comparison of timing of the signal from accelerometer and the reference clock. The resampling function keeps alignment to a reference clock in a sliding window to generate a precise sampling rate. An algorithm calibrates the real time 32 kHz clock (X-Tal) 226. The accelerometer 222 sampling frequency correction processor sets the down-sampling coefficient for each frame of data from the accelerometer signal. The present approach provides tracking the timing of the accelerometer signal continuously and selecting the down-sampling coefficient to minimize the accumulated timing error. That allows continuous accelerometer 222 digital data to align to the accurate clock with high precision.

In one aspect, the reusable electronic module 204 employs a low-power low-memory data storage and transfer scheme. In one aspect, storage and transfer of data in the re-wearable wireless device 102 memory 212 is optimized for low-power and low memory usage. Sensor data is stored as records in the memory 212, each with a type identifier. Records are transferred in a packet payload to an external device by the RF wireless communication circuit 206 in the same format as stored on the wireless wearable sensor 100. Records are stored sequentially with variable length to optimize space usage. A data directory is included which allows fast record read access from the memory 212. A data directory is included which allows fast counting of the data records by type.

In one aspect, the reusable electronic module 204 employs a high-assurance integrity data storage and transfer scheme. The re-wearable wireless device 102 memory storage and transfer scheme is designed for high-assurance data integrity. For each data record stored in the memory 212 of the re-wearable wireless device 102, there is an error-detecting code that can be used to detect data record corruption. When the re-wearable wireless device 102 reads a data record from the memory 212 prior to data packet transfer to the external device, the error-detecting code is checked. When the re-wearable wireless device 102 detects corruption of the stored data record, an error signal is sent to an external device by the RF wireless communication circuit 206. Each packet transferred from the re-wearable wireless device 102 to the external device contains an error-detecting code which can be used by the external device to detect packet corruption.

In one aspect, the signal processing accelerator portion of the ASIC portion 208 includes a computational engine optimized for implementing high efficiency signal processing tasks. In one implementation, signal processing functions are hard coded in logic. Such implementations may be 10× or more efficient compared to software-based algorithms implemented in software running on a processor 210 or microcontroller unit. The efficiency may be in chip sized, power consumption, or clock speed or some combination of all three. Another implementation maintains some level of programmability, but utilizes execution unit(s) that are optimized calculations. One example is an FFT-butterfly engine. The engine may enable FFT calculations for various size data sets, but maintain significant efficiency improvement over software running on a processor 210. The execution units also may be multiply accumulate units (MAC), which are a common DSP function block or could be a floating point calculation unit(s) or FIR filter primitives, etc. In these cases the efficiency for a given integrated circuit process is greater than that of software on a processor 210, but less than that of dedicated hardware, however they are much more flexible.

The signal processing accelerator maintains an interface between the processor 210. This interface may include first-in-first-out (FIFO) registers, dual port memories, the direct memory access (DMA) engine of the processor 210, and/or registers. The interface typically includes some form of contention recognition or avoidance which may be handled at the register-level or at the memory block level. Mechanisms involved may include register flags set, which can be polled by the processor 210 and signal processing accelerator, interrupts to signal either block or delay functions that hold a read or write request until the higher priority device has completed their activity.

In one aspect, the disposable component 202 is coupled to the reusable electronic module 204 on the PCBA with one or more sensors attached for interface to the item to be monitored (person, animal, machine, building, etc.). In one aspect, the disposable component 202 may comprise a flex circuit 228, battery holder or housing (covering) and one or more sensors, including but not limited to ambient and body temperature (temp) 230 (living or not), ECG, GSR/electro-dermal activation (EDA) 232, body composition (50 Hz), SpO2/pulse oximetry, strain gauge, among others. Various algorithms executed by the ASIC portion 208 or the processor 210 provide heat flux, HR, HRV, respiration, stress, ECG, steps, body angle, fall detection, among others.

In one aspect, the flex circuit 228 comprises interface components that electrically interfaces with the electrical circuits on the PCBA. The flex circuit 228 provides a platform for configurability and enables interfacing of multiple sensor configurations to a single physical PCBA and electrically to the reusable electronic module 204. In one aspect, stainless steel domed electrodes 220a, 220b of the GSR/EDA sensor 232 are electrically coupled to the PCBA via the flex circuit 228.

The re-wearable wireless device 102 collects data from various sensors, applies signal processing algorithms to the data collected, stores the resulting information in memory, and forwards data/information to another device using either a wireless or wired connection. The user interface consists of one or two LEDs 214 and a push-button 234.

Power is provided from a primary battery 214, but could also be sourced from a secondary battery. The battery(s) 214 portion of the electronics module of the reusable component 204 may be selected to source peak currents that are adequate to support the cellular radio with rechargeable Li+ or LiPO (lithium polymer or lithium prismatic cells) being the preferred types, but other primary and secondary battery types are contemplated. In some aspects, the disposable component may include a battery, if a primary cell is used. In some aspects, the reusable component may contain the electronics and the battery 214, assuming a secondary cell is used. The re-wearable wireless device 102 may include a re-charger to recharge the re-useable module. The subject 104 may be supplied with multiple re-useable components to ensure continuity of use while the reusable component is being recharged. Device size may be in the 25 cc range for near-term implementations, with the form factor of the re-wearable wireless device 102 shrinking as semiconductor devices and battery technology improves. Battery size may typically be limited by the peak current draw of the mobile chipset, not by capacity. In most use cases, the current draw of the mobile chipset will be limited by disabling/powering off the chip and periodically (a few times per day) powering the chip and transmitting the data.

One of the challenges in putting a cellular radio in re-wearable wireless device 102 is the power source, the battery 214. The cellular radio cellular wireless communication device 206 will draw from about 700 to about 800 milliamps peaked current may be a challenge to accomplish with the battery 214. Rechargeable batteries 214 such as lithium polymer or lithium prismatic cell as the power source can source adequate current under peak loads. Another key feature is having the re-wearable wireless device 102 last for a week or two weeks where typically a cellular phone battery lasts only a couple of days or a few days. To extend the battery life of the re-wearable wireless device 102 from about one week to about three weeks, connection to the Internet 112 (FIG. 1) may be limited to few times per day. The re-wearable wireless device 102 can store the data in the memory 212 and buffer data on board. Therefore, it would be possible to connect to Internet 112 a few times a day, or even up to ten times a day. In between connections to the Internet, the re-wearable wireless device 102 can turn off the wireless communication device 206. In one aspect, the re-wearable wireless device 102 can be placed in a deep sleep state or a sleep state, which consumes only a few micro amps of current instead of hundreds of micro amps or milliamps of current while it is in the idle state.

To smooth out an 800 milliamps peak from a baseline current draw of 100 to 200 milliamps a capacitor may be employed across the battery 214. A large enough capacitor can effectively reduce what the peak load seen by the battery 214. The capacitor may be a super capacitor, for example. Using this technique, for example, a 300 milliamp hour battery may be adequate to source 800 milliamps.

The re-wearable wireless device 102 can come out of the sleep states either on a timing basis or on an event basis. In one aspect, the re-wearable wireless device 102 has its own low power microcontroller which runs on a continuous basis. The event marker detection algorithm, ECG sensing, heart rate sensing, and other physiologic sensing functions run continuously and when the timer expires, it wakes up the wireless communication circuit 206 to connect to the cellular network 108 (FIG. 1) and the Internet 112 (FIG. 1). In another aspect, the wireless communication circuit 206 can come out of the sleep state based on events such as activity data determined by the accelerometer 222, for example. Events or activity, such as the detection of an arrhythmia, would require an immediate down load. Events may include the subject 104 (FIG. 1) pushing the user button 234. In certain circumstances, the event may be lack of activity. Or it may be that the subject 104 has fallen or the data shows an unusual gait via the accelerometer 222. In one aspect, the re-wearable wireless device 102 may comprise microphone device. Accordingly, the wireless communication circuit 206 can be activated based on wheezing events caused by asthma or rapid breathing. Lack of medication could also trigger the wireless communication circuit 206 to come out of sleep mode.

The mobile chipset also may be used as a telephone for voice communication by utilizing a user interface (UI) provided on the re-wearable wireless device 102 to activate/power it and utilizing voice recognition to cause it to dial. The UI may include a push button 234, an accelerometer 222 with pattern recognition capabilities, a speaker, and a microphone.

The disposable component 202 may include electrodes 220a, 220b and one or more types of adhesives for adhering the re-wearable wireless device 102 to the skin of the subject 104 (FIG. 1), which has a typical life of about 3 to about 10 days on most people. The sensor data may include ECG data (via hydrogel electrodes) 220a, 220b, accelerometer data in up to 3 axis, temperature data, adjacent to skin (thermistor), ambient (or case temperature away from body) (thermistor), temperature on the PCBA (silicon device incorporated into the ASIC portion 208), GSR, EDA (discrete stainless-steel electrodes), high-frequency, in-body electric signals—10 KHz and higher, sampled via conduction through the hydrogel skin electrodes (same as ECG).

As shown, the re-wearable wireless device 102 may comprise a memory 212. In various aspects, the memory 212 may comprise any machine-readable or computer-readable media capable of storing data, including both volatile and non-volatile memory. For example, memory may include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

The re-wearable wireless device 102 may comprise a processor 210 such as a central processing unit (CPU). In various aspects, the processor 210 may be implemented as a general purpose processor, a chip multiprocessor (CMP), a dedicated processor, an embedded processor, a digital signal processor (DSP), a network processor, a media processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor also may be implemented by a controller, a microcontroller, an application specific integrated circuit (ASIC), a field programmable gate array (FPGA), a programmable logic device (PLD), and so forth.

In various aspects, the processor 210 may be arranged to run an operating system (OS) and various mobile applications. Examples of an OS include, for example, operating systems generally known under the trade name of Microsoft Windows OS, and any other proprietary or open source OS. Examples of mobile applications include, for example, a telephone application, a camera (e.g., digital camera, video camera) application, a browser application, a multimedia player application, a gaming application, a messaging application (e.g., e-mail, short message, multimedia), a viewer application, and so forth.

In various aspects, the processor 210 may be arranged to receive information through a communications interface. The communications interface may comprises any suitable hardware, software, or combination of hardware and software that is capable of coupling the re-wearable wireless device 102 to one or more networks and/or devices.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as printers.

In various aspects, the communications interface may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the local node 106 may include a wireless interface comprising one or more antennas, transmitters, receivers, transceivers, amplifiers, filters, control logic, and so forth.

In various aspects, the re-wearable wireless device 102 may provide voice and/or data communications functionality in accordance with different types of cellular radiotelephone systems. In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may include various wireless wide area network (WWAN) protocols, such as GSM cellular radiotelephone system protocols with GPRS, CDMA cellular radiotelephone communication systems with 1xRTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, and so forth.

In various implementations, the described aspects may comprise part of a cellular communication system. Examples of cellular communication systems may include CDMA cellular radiotelephone communication systems, GSM cellular radiotelephone systems, North American Digital Cellular (NADC) cellular radiotelephone systems, Time Division Multiple Access (TDMA) cellular radiotelephone systems, Extended-TDMA (E-TDMA) cellular radiotelephone systems, Narrowband Advanced Mobile Phone Service (NAMPS) cellular radiotelephone systems, third generation (3G) wireless standards systems such as WCDMA, CDMA-2000, UMTS cellular radiotelephone systems compliant with the Third-Generation Partnership Project (3GPP), fourth generation (4G) wireless standards, and so forth.

Further, in various aspects, the re-wearable wireless device 102 may incorporate and/or be associated with, e.g., communicate with, various devices. Such devices may generate, receive, and/or communicate data, e.g., physiologic data. The devices include, for example, "intelligent" devices such as gaming devices, e.g., electronic slot machines, handheld electronic games, electronic components associated with games and recreational activities.

In addition to the standard voice function of a telephone, various aspects of mobile telephones may support many additional services and accessories such as short message service (SMS) for text messaging, email, packet switching for access to the Internet, Java gaming, wireless, e.g., short range data/voice communications, infrared, camera with video recorder, and multimedia messaging system (MMS) for sending and receiving photos and video. Some aspects of mobile telephones connect to a cellular network of base stations (cell sites), which is, in turn, interconnected to the public switched telephone network (PSTN) or satellite communications in the case of satellite phones. Various aspects of mobile telephones can connect to the Internet, at least a portion of which can be navigated using the mobile telephones.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, assembly language, machine code, and so forth.

In various aspects, the re-wearable wireless device 102 also functions to communicate, e.g., receive and transmit, non-physiologic data. Example of non-physiologic data include, for example, gaming rules and data generated by a separate cardiac-related device such as an implanted pacemaker and communicated to the hub directly or indirectly.

The re-wearable wireless device 102 may include additional functionality typically found in other mobile device such as, for example, personal communication devices, handheld devices, and mobile telephones. In various aspects, the re-wearable wireless device 102 may comprise functionality found in a handheld portable device, computer, mobile telephone, sometimes referred to as a smartphone, tablet personal computer (PC), kiosk, desktop computer, or laptop computer, or any combination thereof. Examples of smartphones include, for example, products generally known under the following trade designations Blackberry, iPhone, Android, Windows Phone, among others. Although some aspects of the re-wearable wireless device 102 may be described with a mobile or fixed computing device implemented as a smartphone, personal digital assistant, laptop, desktop computer by way of example, it may be appreciated that the various aspects are not limited in this context. For example, a mobile computing device may comprise, or be implemented as, any type of wireless device, mobile station, or portable computing device with a self-contained power source, e.g., battery, such as the laptop computer, ultra-laptop computer, personal digital assistant (PDA), cellular telephone, combination of cellular telephone/PDA, mobile unit, subscriber station, user terminal, portable computer, handheld computer, palmtop computer, wearable computer, media player, pager, messaging device, data communication device, and so forth. A fixed computing device, for example, may be implemented as a desk top computer, workstation, client/server computer, and so forth.

Figure 3:
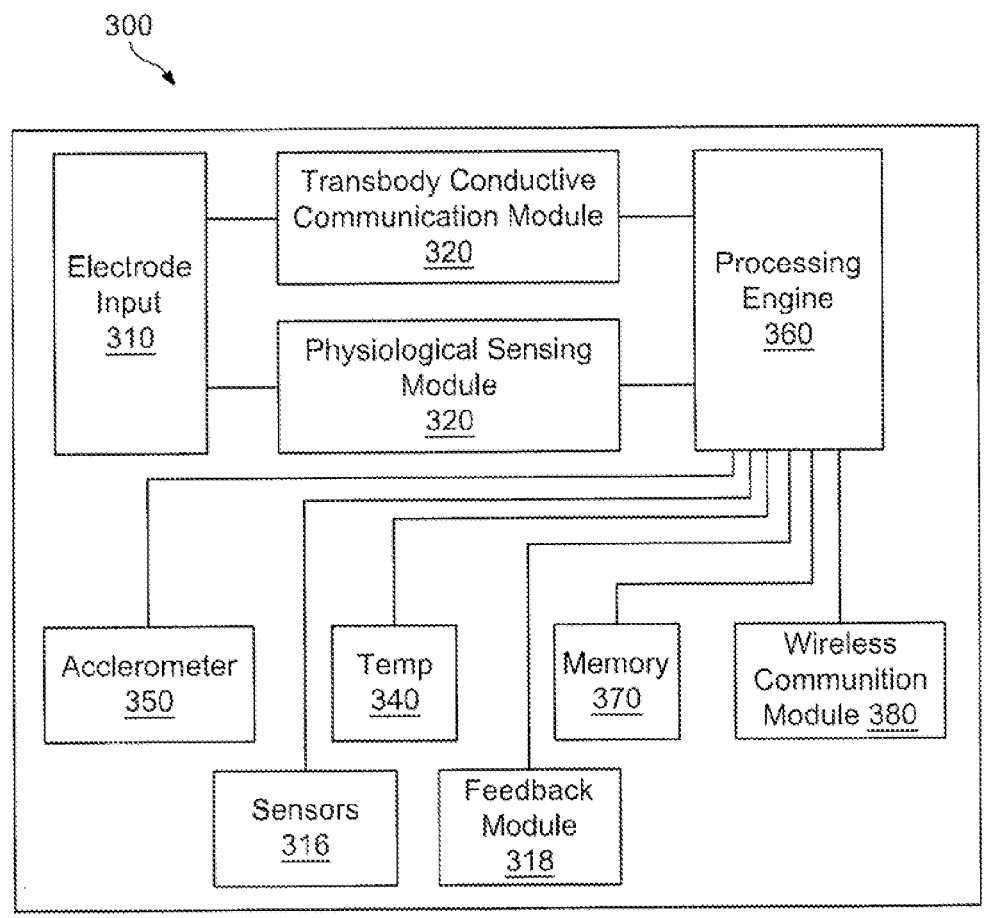
FIG. 3 is a block functional diagram of one aspect of an integrated circuit component of the electronics module of the reusable component re-wearable wireless device shown in FIGS. 1 and 2.

FIG. 3 is a block functional diagram 300 of one aspect of an integrated circuit component of the electronics module of the reusable component 204 re-wearable wireless device 102 shown in FIGS. 1 and 2. In FIG. 3, the electronics module of the reusable component 204 of the re-wearable wireless device 102 comprises an electrode input 310. Electrically coupled to the electrode input 310 are a transbody conductive communication module 320 and a physiological sensing module 330. In one aspect, the transbody conductive communication module 320 is implemented as a first, e.g., high, frequency (HF) signal chain and the physiological sensing module 330 is implemented as a second, e.g., low, frequency (LF) signal chain. Also shown are CMOS temperature sensing module 340 (for detecting ambient temperature) and a 3-axis accelerometer 350. The re-wearable wireless device 102 also comprises a processing engine 360 (for example, a microcontroller and digital signal processor), a non-volatile memory 670 (for data storage), and a wireless communication module 380 comprising a mobile chipset to receive and/or transmit data to and from a cellular communication network. In various aspects, the communication modules 320, 380 may comprise one or more transmitters/receivers ("transceiver") modules. As used herein, the term "transceiver" may be used in a very general sense to include a transmitter, a receiver, or a combination of both, without limitation. In one aspect, the transbody conductive communication module 320 is configured to communicate with an event marker system 420 (FIG. 4).

The sensors 316 typically contact the subject 104 (FIG. 1), e.g., are removably attached to the torso. In various aspects, the sensors 616 may be removably or permanently attached to the re-wearable wireless device 102. For example, the sensors 316 may be removably connected to the re-wearable wireless device 102 by snapping metal studs. The sensors 316 may comprise, for example, various devices capable of sensing or receiving the physiologic data. The types of sensors 316 include, for example, electrodes such as biocompatible electrodes. The sensors 316 may be configured, for example, as a pressure sensor, a motion sensor, an accelerometer, an electromyography (EMG) sensor, an event marker system, a biopotential sensor, an electrocardiogram sensor, a temperature sensor, a tactile event marker sensor, and an impedance sensor.

The feedback module 318 may be implemented with software, hardware, circuitry, various devices, and combinations thereof. The function of the feedback module 318 is to provide communication with the subject 104 (FIG. 1) in a discreet, tactful, circumspect manner as described above. In various aspects the feedback module 318 may be implemented to communicate with the subject 104 using techniques that employ visual, audio, vibratory/tactile, olfactory, and taste.

Figure 4:
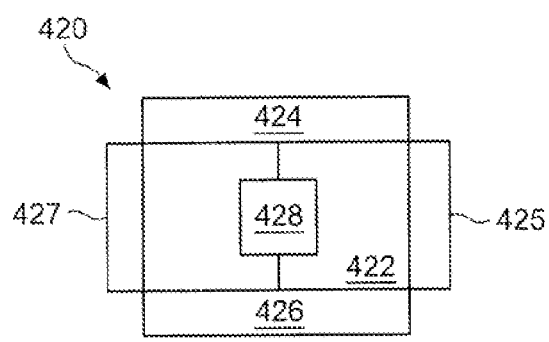
FIG. 4 shows one aspect of an event marker system.

FIG. 4 shows one aspect of an event marker system 420. In various aspects the event marker system 420 can be used in association with any medication product, as mentioned above, to determine the origin of the medication and to confirm that at least one of the right type and the right dosage of medication was delivered to the patient and in some aspects to determine when a patient takes the medication product. The scope of the present disclosure, however, is not limited by the environment and the medication product that may be used with the system 420. For example, the system 420 may be activated either in wireless mode, in galvanic mode by placing the system 420 within a capsule and then placing the capsule within a conducting fluid, or a combination thereof, or exposing the system 420 to air. Once placed in a conducting fluid, for example, the capsule would dissolve over a period of time and release the system 420 into the conducting fluid. Thus, in one aspect, the capsule would contain the system 420 and no product. Such a capsule may then be used in any environment where a conducting fluid is present and with any product. For example, the capsule may be dropped into a container filled with jet fuel, salt water, tomato sauce, motor oil, or any similar product. Additionally, the capsule containing the system 420 may be ingested at the same time that any pharmaceutical product is ingested in order to record the occurrence of the event, such as when the product was taken.

In the specific example of the system 420 combined with a medication or pharmaceutical product, as the product or pill is ingested, or exposed to air, the system 420 is activated in galvanic mode. The system 420 controls conductance to produce a unique current signature that is detected by the re-wearable wireless device 102, for example, thereby signifying that the pharmaceutical product has been taken. When activated in wireless mode, the system controls modulation of capacitive plates to produce a unique voltage signature associated with the system 420 that is detected.

In one aspect, the system 420 includes a framework 422. The framework 422 is a chassis for the system 420 and multiple components are attached to, deposited upon, or secured to the framework 422. In this aspect of the system 420, a digestible material 424 is physically associated with the framework 422. The material 424 may be chemically deposited on, evaporated onto, secured to, or built-up on the framework all of which may be referred to herein as "deposit" with respect to the framework 422. The material 424 is deposited on one side of the framework 422. The materials of interest that can be used as material 424 include, but are not limited to: Cu, CuCl, or CuI. The material 424 is deposited by physical vapor deposition, electrodeposition, or plasma deposition, among other protocols. The material 424 may be from about 0.05 to about 500 μm thick, such as from about 5 to about 100 μm thick. The shape is controlled by shadow mask deposition, or photolithography and etching. Additionally, even though only one region is shown for depositing the material, each system 420 may contain two or more electrically unique regions where the material 424 may be deposited, as desired.

At a different side, which is the opposite side as shown in FIG. 7, another digestible material 426 is deposited, such that the materials 424, 426 are dissimilar and insulated from each other. Although not shown, the different side selected may be the side next to the side selected for the material 424. The scope of the present disclosure is not limited by the side selected and the term "different side" can mean any of the multiple sides that are different from the first selected side. In various aspects, the dissimilar material may be located at different positions on a same side. Furthermore, although the shape of the system is shown as a square, the shape may be any geometrically suitable shape. The materials 424, 426 are selected such that they produce a voltage potential difference when the system 420 is in contact with conducting liquid, such as body fluids. The materials of interest for material 426 include, but are not limited to: Mg, Zn, or other electronegative metals. As indicated above with respect to the material 424, the material 426 may be chemically deposited on, evaporated onto, secured to, or built-up on the framework. Also, an adhesion layer may be necessary to help the material 426 (as well as material 724 when needed) to adhere to the framework 722. Typical adhesion layers for the material 426 are Ti, TiW, Cr or similar material. Anode material and the adhesion layer may be deposited by physical vapor deposition, electrodeposition or plasma deposition. The material 426 may be from about 0.05 to about 500 μm thick, such as from about 5 to about 100 μm thick. However, the scope of the present disclosure is not limited by the thickness of any of the materials nor by the type of process used to deposit or secure the materials to the framework 422.

According to the disclosure set forth, the materials 424, 426 can be any pair of materials with different electrochemical potentials. Additionally, in the embodiments wherein the system 420 is used in-vivo, the materials 424, 426 may be vitamins that can be absorbed. More specifically, the materials 424, 426 can be made of any two materials appropriate for the environment in which the system 420 will be operating. For example, when used with an ingestible product, the materials 424, 426 are any pair of materials with different electrochemical potentials that are ingestible. An illustrative example includes the instance when the system 420 is in contact with an ionic solution, such as stomach acids. Suitable materials are not restricted to metals, and in certain embodiments the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in TABLE 1 below. In one embodiment, one or both of the metals may be doped with a non-metal, e.g., to enhance the voltage potential created between the materials as they come into contact with a conducting liquid. Non-metals that may be used as doping agents in certain embodiments include, but are not limited to: sulfur, iodine, and the like. In another embodiment, the materials are copper iodine (CuI) as the anode and magnesium (Mg) as the cathode. Aspects of the present disclosure use electrode materials that are not harmful to the human body.

TABLE 1

|  | Anode | Cathode |
|---|---|---|
| Metals | Magnesium, Zinc Sodium (†), Lithium (†) | Iron |
| Salts |  | Copper salts: iodide, chloride, bromide, sulfate, formate, (other anions possible) $Fe^{3+}$ salts: e.g. orthophosphate, pyrophosphate, (other anions possible) Oxygen (††) on platinum, gold or other catalytic surfaces |
| Intercalation compounds | Graphite with Li, K, Ca, Na, Mg | Vanadium oxide Manganese oxide |

Thus, when the system 420 is in contact with the conducting fluid, a current path is formed through the conducting fluid between the dissimilar materials 424, 426. A control device 428 is secured to the framework 422 and electrically coupled to the materials 424, 426. The control device 428 includes electronic circuitry, for example control logic that is capable of controlling and altering the conductance between the materials 424, 426.

The voltage potential created between the dissimilar materials 424, 426 provides the power for operating the system as well as produces the current flow through the conducting fluid and the system 420. In one aspect, the system 420 operates in direct current mode. In an alternative aspect, the system 420 controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the dissimilar materials 424, 426 is completed external to the system 420; the current path through the system 420 is controlled by the control device 428. Completion of the current path allows for the current to flow and in turn a receiver, not shown, can detect the presence of the current and recognize that the system 420 has been activate and the desired event is occurring or has occurred.

In one embodiment, the two dissimilar materials 424, 426 are similar in function to the two electrodes needed for a direct current power source, such as a battery. The conducting liquid acts as the electrolyte needed to complete the power source. The completed power source described is defined by the physical chemical reaction between the dissimilar materials 424, 426 of the system 420 and the surrounding fluids of the body. The completed power source may be viewed as a power source that exploits reverse electrolysis in an ionic or a conduction solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, the two dissimilar materials 424, 426 are shielded from the surrounding environment by an additional layer of material. Accordingly, when the shield is dissolved and the two dissimilar materials 424, 426 are exposed to the target site, a voltage potential is generated.

In certain aspects, the complete power source or supply is one that is made up of active electrode materials, electrolytes, and inactive materials, such as current collectors, packaging. The active materials are any pair of materials with different electrochemical potentials. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain embodiments, electrode materials are chosen to provide for a voltage upon contact with the target physiological site, e.g., the stomach, sufficient to drive the system of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

Referring still to FIG. 4, the dissimilar materials 424, 426 provide the voltage potential to activate the control device 428. Once the control device 428 is activated or powered up, the control device 428 can alter conductance between the first and second materials 424, 426 in a unique manner. By altering the conductance between the first and second materials 424, 426, the control device 428 is capable of controlling the magnitude of the current through the conducting liquid that surrounds the system 420. This produces a unique current signature that can be detected and measured by a receiver (not shown), which can be positioned internal or external to the body. The receiver is disclosed in greater detail in U.S. patent application Ser. No. 12/673,326 entitled "BODY-ASSOCIATED RECEIVER AND METHOD" filed on Dec. 15, 2009, and published as 2010-0312188 A1 dated Dec. 9, 2010 which is incorporated herein by reference in its entirety. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "IN-BODY DEVICE WITH VIRTUAL DIPOLE SIGNAL AMPLIFICATION" filed Sep. 25, 2008, the entire content of which is incorporated herein by reference. Alternatively, throughout the disclosure herein, the terms "non-conducting material," "membrane," and "skirt" are interchangeably used with the term "current path extender" without impacting the scope or the present embodiments and the claims herein. The skirt, shown in portion at 425, 427, respectively, may be associated with, e.g., secured to, the framework 422. Various shapes and configurations for the skirt are contemplated as within the scope of the various aspects of the present invention. For example, the system 420 may be surrounded entirely or partially by the skirt and the skirt maybe positioned along a central axis of the system 120 or off-center relative to a central axis. Thus, the scope of the present invention as claimed herein is not limited by the shape or size of the skirt. Furthermore, in other embodiments, the dissimilar materials 424, 426 may be separated by one skirt that is positioned in any defined region between the dissimilar materials 424, 426.

The system 420 may be grounded through a ground contact. The system 420 also may include a sensor module. In operation, ion or current paths are established between the first material 424 to the second material 426 and through a conducting fluid in contact with the system 420. The voltage potential created between the first and second materials 424, 426 is created through chemical reactions between the first and second materials 424, 426 and the conducting fluid. In one aspect, the surface of the first material 424 is not planar, but rather an irregular surface. The irregular surface increases the surface area of the material and, hence, the area that comes in contact with the conducting fluid.

In one aspect, at the surface of the first material 424, there is chemical reaction between the material 424 and the surrounding conducting fluid such that mass is released into the conducting fluid. The term mass as used herein refers to protons and neutrons that form a substance. One example includes the instant where the material is CuCl and when in contact with the conducting fluid, CuCl becomes Cu (solid) and Cl— in solution. The flow of ions into the conduction fluid is via ion paths. In a similar manner, there is a chemical reaction between the second material 426 and the surrounding conducting fluid and ions are captured by the second material 426. The release of ions at the first material 424 and capture of ion by the second material 426 is collectively referred to as the ionic exchange. The rate of ionic exchange and, hence the ionic emission rate or flow, is controlled by the control device 428. The control device 428 can increase or decrease the rate of ion flow by altering the conductance, which alters the impedance, between the first and second materials 424, 426. Through controlling the ion exchange, the system 420 can encode information in the ionic exchange process. Thus, the system 420 uses ionic emission to encode information in the ionic exchange.

The control device 428 can vary the duration of a fixed ionic exchange rate or current flow magnitude while keeping the rate or magnitude near constant, similar to when the frequency is modulated and the amplitude is constant. Also, the control device 428 can vary the level of the ionic exchange rate or the magnitude of the current flow while keeping the duration near constant. Thus, using various combinations of changes in duration and altering the rate or magnitude, the control device 428 encodes information in the current flow or the ionic exchange. For example, the control device 428 may use, but is not limited to any of the following techniques namely, Binary Phase-Shift Keying (PSK), Frequency Modulation (FM), Amplitude Modulation (AM), On-Off Keying, and PSK with On-Off Keying.

Various aspects of the system 420 may comprise electronic components as part of the control device 428. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

The system 420 controls the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the system 420 is capable of producing various different unique exchanges or signatures and, thus, provides additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

FIGS. 5-10 illustrate various aspects of re-wearable wireless devices. The re-wearable wireless device comprises a reusable component and a disposable component. The reusable component generally comprises an electronics module and a power source. The disposable component generally comprises skin electrodes and skin adhesive.

The electronics module is a durable component, meaning its lifetime exceeds that of some or all of the remaining components. The electronics module lifetime may range up to several years. The skin adhesive is a consumable component with a lifetime less than its useable lifetime is less than that for the durable components. Typical lifetimes for the skin adhesive may range from less than 24 hours to 14 days or more. The skin electrodes and power source may be either durable or consumable components depending on the technology selected to implement those components. The lifetime for skin electrodes may range from less than 24 hours to years, depending on the type. The power source may have a lifetime of less than 24 hours to years depending on type. The electronics, electrodes and power source are all considered electrical or electronic components. The re-wearable wireless device also includes one other feature, means to interconnect the electronic components.

The re-wearable wireless device permits user replacement of the consumable components, permitting the high cost components, the durable component(s) to be used repeatedly, lowering the overall cost of use for the system. FIGS. 5-10 illustrate three aspects of re-wearable wireless devices: a snap-in module, an overlay module, and a wire module.

FIGS. 5-7 illustrate one aspect of a snap-in module type re-wearable wireless device comprising a reusable component and a disposable component configured to be secured to a user via an adhesive layer. FIG. 5 illustrates one aspect of a disposable component 500 comprising an adhesive base 502, electrodes 504a, 504b (shown in phantom), electrical contacts 506a, 506b, and a mechanical snap-in connect mechanism 508. The electrodes 504a, 504b are electrically coupled to the electrical contacts 506a, 506b. The mechanical snap-in connect mechanism 508 comprises projecting elements 510a, 510b projecting at right angles toward a center portion of the mechanical snap-in connect mechanism 508.

FIG. 6 is a perspective top view of one aspect a reusable component 600 comprising an electronics module located within a housing 602 configured to mate with the mechanical snap-in connect mechanism 508 of the disposable component 500 shown in FIG. 5. The housing 602 of the reusable component 600 comprises depressions 604a, 604b (not shown) formed in the housing 602 to engage the respective projecting elements 510a, 510b such that the reusable component 600 snaps into the mechanical snap-in connect mechanism 508 and is retained thereby.

FIG. 7 is a perspective bottom view of one aspect of a reusable component 600. A bottom portion 606 of the reusable component 600 comprises electrical contacts 702a, 702b, which are configured to electrically couple to the electrical contacts 506a, 506b in the mechanical snap-in connect mechanism 508. Accordingly, electrical signals detected by the electrodes 504a, 504b are coupled to the electronics module of the reusable component through the electrical contacts 702a, 702b. The electronics module is located within the housing 602 of the reusable component 600. The electronics module is functionally equivalent to the electronics modules shown in FIGS. 2-3. In addition, the bottom portion 606 of the reusable component 600 may further comprises a communication channel I/O Address 704a and PIN 704b that uniquely identifies the electronics module of the reusable component 600. Modern wireless communications between two devices requires exchange of an address and a PIN to establish a link. The I/O Address and PIN 608 may be provided on a label, directly printed on the bottom portion 606 or other part of the housing 602, or any other suitable means.

The reusable component 600 comprising the electronics module is a durable device and the adhesive base 502 and electrodes 504a, 504b are consumable. The power source—battery—may be either consumable or durable. If the battery is packaged in the skin adhesive base 502 envelope, then it is a consumable. A LiMn coin cell would typically be used with capacity matched to ensure battery lifetime comparable to the skin adhesive base 502. Alternatively, the battery may be a durable component packaged with the electronics module. A rechargeable battery could be used and means to recharge the battery must be provided—either through a connector or via inductive coil. A primary battery could also be used since the electronics module is otherwise low power, and primary batteries provide significantly greater energy density than a secondary battery. Electrical means to connect the disposable component 500 and the reusable component 600 are provided by electrical spring contacts 506a, 506b, 702a, 702b integrated into the respective components.

The disposable component 500 may be constructed of a flex circuit for interconnection and to form the electrodes 504a, 504b in conjunction with one or more hydrogel. The housing 602 of the reusable component 600 comprises a plastic component and provides means to latch the electronics module onto the adhesive base 502 and the entire reusable component 600 is housed by closed-cell foam. The skin adhesive base 502 is likely a composite type with a hydro-colloid as the primary adhesive with an acrylic type provided to hold the re-wearable wireless device on while the hydro-colloid activates and to also avoid having the hydro-colloid ooze out of the side of the re-wearable wireless device.

FIGS. 8 and 9 illustrate one aspect of a re-wearable wireless device comprising a reusable component 800 and a disposable component 900 configured to be secured to a user via an adhesive overlay 902. FIG. 8 illustrates one aspect of a reusable component 800 and FIG. 9 illustrates one aspect of an adhesive overlay 902. The re-wearable wireless device shown in FIGS. 8 and 9, the durable reusable component 800 comprises the electronics module, skin electrodes 802a, 802b, and power source form the and the disposable component 900 only the skin adhesive overlay 902. There is no electrical interconnect outside the reusable component 800. The power source may be implemented as described in connection with FIGS. 5-7 for the snap-in module. Electrodes 802a, 02b may be dry or capacitive type. In this case the skin adhesive overlay 902 may comprise a 3-piece composite with a center section 904 configured to hold the reusable component 800 comprising the electronics module in place, but not create a sticky build up on the module, an hydrocolloid for primary skin adhesion and an acrylic with function as described above.

FIG. 10 illustrates one aspect of a re-wearable wireless device comprising a reusable component 1000 and a disposable component 1002. Electrodes 1004a, 1004b are attached to a subject. The electrodes 1004a, 1004b are attached to an electronics module of the reusable component 1000 via corresponding electrode terminals 1006a, 1006b. The re-wearable wireless device shown in FIG. 10, In this case the electronics and power source are durable. The skin electrodes and adhesive are consumable. The electronics and power source are packaged in the reusable component 1000 housing 1008 such that it adheres to clothing the subject is otherwise wearing instead of to the skin via adhesive. Most commonly this will be done via a spring clip, but other means such as Velcro or adhesive could be used. As illustrated in FIG. 10, common ECG electrodes 1004a, 1004b may be employed in combination with the electronics module to form the re-wearable wireless device. Alternatively, the electrodes 1004a, 1004b could be integrated into a single unit which ensures proper spacing of the electrodes 1004a, 1004b. Interconnection between the electrodes 1004a, 1004b and the electronics module is provided by a 2-conductor cable 1010a, 1010b coupled to corresponding electrode terminals 1006a, 1006b. A connector 1012 is coupled to a plug receptacle in the electronics module, or the connection may be fixed. The connector 1012 may be provided on either end of the cable.

Figure 11:
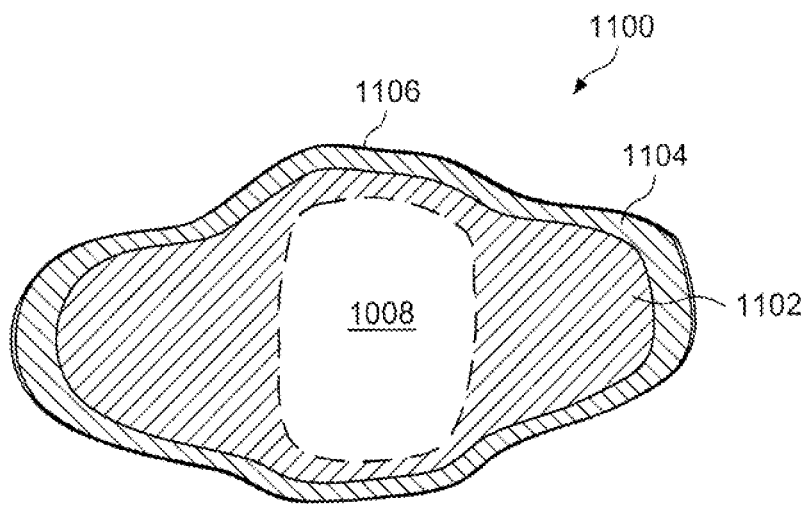
FIG. 11 illustrates one aspect of an adhesive base to be secured to the subject.

FIG. 11 illustrates one aspect of an adhesive base 1100 to be secured to the subject. The adhesive base 1100 may be used in conjunction with any of the re-wearable wireless devices disclosed herein. Adhesion and length of adhesion of any adhesive based wearable device can be affected by different level of sensitivity, different skin types, activity levels, and body shape of the subject. Accordingly, in one aspect, the adhesive base 1100 comprises an adhesive system that at the same time does not irritate the skin of the user, is comfortable to wear, is not too large, remains attached for the design lifetime, regardless of user variability, and is simple to apply to the user by the user.

In one aspect, the adhesive base 1100 for a reusable wearable device is configured with an adhesive system that uses two different adhesive layers 1102, 1104 to accomplish these functionalities. A primary adhesive layer 1102 is a hydrocolloid adhesive which is known to be very mild to the skin of users and can be easily tolerated my most users for periods of time extending beyond about 7 days. The primary adhesive layer 1102 does not, however, have the most durable attachment to the skin and is susceptible to excessive water absorption. A secondary adhesive layer 1104 is used to partially cover the primary adhesive layer 1102 to create a perimeter around the hydrocolloid based primary adhesive layer 1102. The secondary adhesive layer 1104 is configured to have a stronger adhesive force to the skin and serves to keep the edges 1106 of the adhesive base 1100 from peeling away from the skin. In one aspect, the primary adhesive layer 1102 is distributed over a surface area that is greater than the surface area over which the secondary adhesive layer 1104 is distributed over. The outer secondary adhesive 1104 is the key to long wear times. If this outer perimeter remains intact, the patch can remain attached for about 7 to about 14 days.

As described above, each user and their activities can affect the adhesion of the perimeter 1106 of adhesive. Therefore, the adhesive base 1100 may be employed as a disposable component of a reusable wearable device that includes a base hydrocolloid primary adhesive layer 1102 component and a secondary adhesive layer 1104 component that is added to the reusable wearable device to create an edge seal and attach the adhesive base 1100 to the user. The secondary adhesive layer 1104 may be acrylic based or cyanoacrylate based if a more permanent bond is used. Other secondary adhesive layers 1104 may be employed without limitation. The secondary adhesive 1104 may be provided to the subject as an accessory. Each reusable wearable device can be supplied with multiple secondary adhesive layer 1104 strips to allow for easy replacement and reattaching of the reusable wearable device. The secondary adhesive layer 1104 also can be supplied in different versions with different levels of adhesive and different amounts of adhesive surface area to accommodate different use requirements. This will enable the reusable wearable device to be worn and used for as long as the battery will allow based on programming. In one aspect, the adhesive base 1100 may be adapted and configured to be employed with the reusable wearable device shown in FIGS. 5-7. In another aspect, with the addition of the overlay portion 1108, shown in phantom to indicate that it is optional, the adhesive base 1100 may be adapted and configured to be employed with the reusable wearable device shown in FIGS. 8-9.

In various aspects, the reusable wearable devices described in connection with FIGS. 1, 2, and 6-12 the described throughout this disclosure, the disposable component and the reusable component may be interconnected in a variety of suitable techniques. For example, the disposable component and the reusable component may be interconnected by way of a Zebra connector, surface mount technology (SMT) battery connectors, cellular/mobile phone battery connector concept, flexing battery connects on EM, non-directional seal connections with conductive rubber, hook-and-loop connectors commonly referred to in commerce as Velcro connections and Velcro pins, and a stabbing connector comprising simple electrode surface traces on the disposable component, wherein a thumbtack is stabbed through the trace, wherein the tip of the thumbtack enters the module, and wherein the head of the thumbtack acts as an electrode.

Figure 12B:
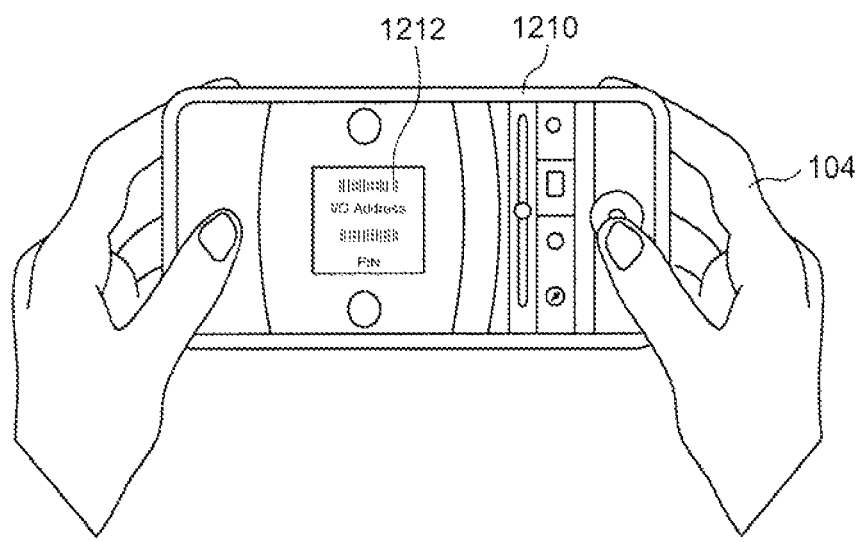

FIG. 12 A is a diagram illustrating a process of capturing an image of the communication channel I/O Address 1204*a* and PIN 1204*b* located on a bottom portion 1202 of a reusable component 1200. In certain aspects, a reusable wearable wireless device such as the reusable component 1200, may not include a cellular phone chipset, as previously discussed, and may contain only a short range radio to provide wireless communication. In such implementations, the short range radio in the electronics module of the reusable component 1200 is configured to exchange information with a local cellular phone, or other local wireless communication device, in order to access wide area networks such as the cellular network 108, the Internet 112, other networks 110 in order to access the remote server 106, as described in connection with FIG. 1. The short range radio in the electronics module of the reusable component 1200 must be paired with the local cell phone in order for the two devices to communicate without interference. Most modern wireless communications between two devices requires exchange of an I/O address 1204*a* and a PIN 1204*b* to establish an authenticated encrypted link. An example of this is Bluetooth, where the address uniquely identifies the device in an environment where many similar devices might be operating. That is how multiple people while in the same room can simultaneously use different Bluetooth headsets without interference. The PIN 1204*b* adds a level of security to prevent fraudulent use of the hardware device, e.g., headset, to dial clandestine telephone calls. Accordingly, the reusable component 1200 of the wearable wireless device includes the I/O Address 1204*a* and PIN 1204*b* associated with the short range radio.

In accordance with various aspects of the present disclosure, a reusable component 1200 equipped with a short range radio can use a wireless link to download data from the cellular network 108 and from there connect to other networks 110 or the Internet 112, as discussed in detail in connection with FIG. 1. Although currently Bluetooth is a common and widely available short range radio wireless standard available in cellular telephones, it is contemplated that in the future standards such as BLE may be common. Accordingly, the present disclosure should not be limited in this context.

In one aspect, the electronics module of the reusable component 1200 may be paired to a cellular telephone in order for the electronics module to access external networks 108, 110, 112 or the remote server 106. This communication may be a weekly exercise, assuming the reusable component 1200 has at least one week of lifetime. Currently, to make a wireless wearable device discoverable, the subject is charged with the task of activating the wireless wearable device to a cellular telephone by pressing an external button switch, making the wireless wearable device discoverable. Once the button is pressed, the short range radio broadcasts its I/O Address 1204*a* and PIN 1204*b* to whatever devices are in range. Then the subject manually selects the I/O Address from a list of devices discovered in the area and copies the PIN 1204b from a label 1214 on the wearable electronics module (or from its package) and enters it into the cellular phone using the keypad/keyboard on the phone and an encrypted link is created between the devices on that basis. Because the manual technique of entering the I/O Address 1204a and PIN 1204b is inherently prone to error and frustration when the I/O Address 1204a and PIN 1204b are misentered and the pairing fails. Alternatively, based only on a broadcasted I/O Address 1204a an unencrypted link may be created between the two devices and used to exchange the PIN 1204b. The PIN 1204b is used to create an encrypted link which is used for further communications. The risk is the exchange on PIN 1204b can be intercepted and the secure link may be compromised.

To overcome certain limitations inherent with this manual process, in one aspect, a new technique is provided as shown in FIG. 12 B, where a camera phone 1210 is employed to capture an image 1212 of the I/O Address 1204 and, optionally, the PIN 1204. The I/O Address 1204 and, optionally, the PIN 1204 are located on the reusable component 1200 as an insignia in a form that is recognizable by machine, human, or combinations thereof. As shown in FIG. 12, the I/O Address and PIN are provided on a label, which is attached to a bottom portion 1202 of the reusable component 1200. It will be appreciated that most modern cellular telephones (smartphones) include fairly high resolution built-in image sensors/cameras and are fairly powerful computing devices, a smartphone 1210 (or suitable cellular telephone) equipped with a built-in camera and, thus, may be employed to capture an image 1212 of the I/O Address and PIN 1204.

In one aspect of the proposed pairing scheme, the subject 104 uses the smartphone 1210 camera to capture an image 1212 of the label 1214 on the reusable component 1200. The label 1214 may have both the device I/O Address 1204a and PIN 1204b or just the PIN 1204b printed on it. The printing may be human readable characters or may be machine readable characters such as bar codes or quick response (QR) codes. A pairing software application running on the smartphone 1210 uses an optical character recognition (OCR) algorithm to convert the captured image 1212 into data—the device I/O Address 1204a and/or the PIN 1204b, thus extracting the pin from the captured image 1212 by the OCR software. The application might also use pattern recognition algorithms to aid the operator in diagnosing errors in the pairing process. For example, if the label or device outline is too small in the image field, then the camera is too far away from the device. If no label or device outline is recognized, then the reusable component 1200 is not located in front of the smartphone 1210 camera or is too close to the smartphone 1210 camera. Once the smartphone 1210 obtains the I/O Address 1204a and PIN 1204b for the reusable component 1200, pairing can be completed securely without further manual intervention from the subject 104.

Receivers may include a signal receiver element which serves to receive the conductively transmitted signal, such as a signal emitted by an identifier of an ingestible event marker. The signal receiver may include a variety of different types of signal receiver elements, where the nature of the receiver element necessarily varies depending on the nature of the signal produced by the signal generation element. In certain aspects, the signal receiver element may include one or more electrodes for detecting signal emitted by the signal generation element, such as two or more electrodes, three or more electrodes, etc. In certain aspects, the receiver device will be provided with two or three electrodes that are dispersed at some distance from each other. This distance allows the electrodes to detect a differential voltage. The distance may vary, and in certain aspects ranges from 0.1 cm to 1.0 m, such as 0.1 to 5 cm, such as 0.5 to 2.5 cm, where the distance 1 cm in some instances.

An example of an external signal receiver aspect of a receiver of interest is shown in FIG. 13. FIG. 13 shows receiver 1001 that is configured to be placed on an external topical location of a subject, such as a chest area. The receiver includes an upper housing plate 1110 (such as may be fabricated from a suitable polymeric material), and includes a manually depressible operation button 1020 and a status identifier LED 1030, which may be used to relay to an observer that the receiver is operating. Manually depressible operation button 1020 can be manually manipulated to transition the receiver from a storage mode to a non-storage mode. When the receiver is in the storage mode, a micro-controller of the receiver may remain in a low duty cycle active state at all times to process input from the on/off button, and the digital signal processor (DSP) of the receiver powered off. When the on/off button is depressed to turn on the receiver, the micro-controller de-bounces the input and powers the DSP into its idle state. While in storage mode, the device may draw less than 10 μA, including 5 μA of current or less, such as 1 μA or less and including 0.1 μA or less. This configuration enables the device to remain at greater than 90% useful battery life if stored for one month (assuming the presence of a 250 mAH battery). Such a button may also be employed for other functions. For example, such a button may be employed to instruct the receiver to obtain certain types of data. In addition or alternatively, such a button may be employed to manually instruct the receiver to transfer data to another device.

FIG. 14 provides an exploded view of the receiver shown in FIG. 13. As shown in FIG. 14, receiver 1001 includes upper housing plate 1110, rechargeable battery 1101, integrated circuit component 1120, and bottom housing plate 1130. Bottom housing plate 1130 snap fits into upper housing plate 1110 to seal the battery and integrated circuit components, 1101 and 1120, in a fluid tight housing. While a snap-fit interaction is illustrated, any convenient mating scheme may be employed, such that the top and bottom housing plates may interact via inter-locking grooves, may be held together via a suitable adhesive, may be welded together, etc. In some instances, the electrical components may be molded into the top and/or bottom housing plates. Also shown is adhesive patch 1140 which snaps into upper housing plate 1110 and includes conductive studs 1141 to 1143, which studs serve as electrode contacts with the body during receiver use. In the receiver, studs 1141 to 1143 are in electrical contact with integrated circuit component 1120, e.g. via wires or other conductive members associated with the upper housing 1150. In one instance, upper housing plate 1110 includes conductive members configured to receive studs 1141 to 1143 coupled to wires (not shown) which in turn provide electrical connection to the integrated circuit component 1120.

FIG. 15 provides an exploded view of adhesive patch 1140. Adhesive patch 1140 includes upper studs 1141, 1142 and 1143, as described above. These studs are in electrical contact with skin contact studs 1151, 1152 and 1153. On the skin side surface of skin contact studs 1151, 1152 and 1153 is a conductive hydrogel layer 1154. Around each stud 1151, 1152 and 1153 are non-conductive hydrogel 1155 and pressure sensitive adhesive 1156 components. In this portion, any convenient physiologically acceptable adhesive may be employed. In some instances, adhesive that chance their adhesive properties in response to an applied stimulus are employed. For example, adhesives that become less adhesive upon application of light, e.g., UV light, or a chemical, may be employed, so that the adhesive remains strong while it is desired for the receiver to remain associated with the body but is readily weakened to facilitate removal of the receiver from the body when desired. On the non-skin side of each skin contact stud is a layer of dry electrode material, such as Ag/AgCl. On the upper surface of this layer of dry electrode material is a porous layer, such as a carbon vinyl layer. Also shown are upper backing layers 1180. Though not shown, upper studs 1141 to 1143 are in electrical contact through the backing layers 1180 (for example urethane and polyethylene) with the dry electrode and skin contact studs which are positioned beneath each upper stud. As illustrated, the studs are off center with respect to their dry electrode layer in the direction of the outer edge of the patch in a manner sufficient to increase dipole size between any two given studs. In addition, where desired a conductivity gradient may be associated with each stud, e.g., by altering the pattern of the porous layer 1170 and/or modifying the composition of the dry electrode layer. Of interest in such aspects is where a conductivity gradient increases in conductivity in the direction of the outer edge of the patch.

FIGS. 16A to 16E provide various views of an alternative external patch configuration 1300 which includes two electrodes 1310 and 1320 in a flexible structure having an adhesive bandage configuration. Patch 1300 includes upper flexible outer support 1330 and bottom flexible support 1350 which fit together as shown in FIG. 16E to enclose an integrated circuit/battery component 1360 and electrodes 1310 and 1320. As shown in FIG. 16D, the bottom surfaces of electrodes 1310 and 1320 are exposed. As shown in FIG. 16E, electrodes 1310 and 1320 include lead elements 1375 and 1370 which provide for electrical contact between the electrodes and the integrated circuit/battery component 1360. Any convenient adhesive component may be employed, such as those described above.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

While certain features of the aspects have been illustrated as described herein, many modifications, substitutions, changes and equivalents will now occur to those skilled in the art. It is therefore to be understood that the appended claims are intended to cover all such modifications and changes as fall within the true spirit of the aspects.

The invention claimed is:

1. A device comprising:
a disposable component comprising:
   a mechanical snap-in connect mechanism comprising:
      a base portion comprising a first electrical contact and a second electrical contact; and
      a pair of projecting elements that are connected to the base portion and extend from the base portion, wherein the pair of projecting elements extend along opposite edges of the base portion and are substantially parallel to each other, and the first and second electrical contacts are arranged between the projecting elements and along a line substantially parallel to the projecting elements; and
   a first electrode electrically coupled to the first electrical contact and a second electrode electrically coupled to the second electrical contact, wherein the first electrode and the second electrode are configured to be secured to a living subject; and
a reusable component configured to operably engage the projecting elements and configured to be secured to the disposable component when the reusable component is engaged with the projecting elements and at least a portion of the reusable component is located between the projecting elements, the reusable component comprising:
   a sensor interface configured to receive signals from the first and the second electrodes configured to be secured to the living subject and monitor one or more physiological and physical parameters associated with the living subject, wherein the sensor interface comprises a third electrical contact and a fourth electrical contact on a surface of the reusable component, wherein the third and fourth electrical contacts are arranged such that when the reusable component is attached to the disposable component, the third electrical contact is coupled to the first electrical contact, and the fourth electrical contact is coupled to the second electrical contact;
   a cellular wireless communication circuit; and
   a transbody conductive communication module configured to communicate with an event maker system in a body of the living subject.

2. The device of claim 1, wherein the reusable component comprises a housing and a depression formed in the housing to couple to the mechanical snap-in connect mechanism to the reusable component.

3. The device of claim 1, wherein the disposable device comprises an adhesive layer to adhere the disposable component to a living subject.

4. The device of claim 1, wherein the disposable component comprises an overlay layer comprising:
   a non-adhesive portion configured to cover the reusable component; and
   an adhesive portion configured to adhere the disposable component to a living subject.

5. The device of claim 1, wherein the reusable component comprises an electrical plug receptacle to electrically couple the at least one electrode to the reusable component.

6. The device of claim 1, wherein the disposable component comprises:
   a first adhesive layer; and
   a second adhesive layer partially covering the first adhesive layer around a perimeter of the first adhesive layer, wherein the first adhesive layer comprises a first adhesive and the second adhesive layer comprises a second adhesive.

7. The device of claim 1, wherein the first and second electrical contacts are arranged on opposite sides of the base portion.

8. The device of claim 1, wherein the reusable component further comprises an identifiable insignia.

9. The device of claim 8, wherein the identifiable insignia is positioned on a surface of the reusable component facing the disposable component when the reusable component is attached to the disposable component.

10. The device of claim 8, wherein the identifiable insignia comprises a communication channel I/O address.

11. The device of claim 1, wherein the reusable component further comprises a housing comprising a pair of corresponding depressions, wherein each projecting element comprises an end portion, and wherein the end portions of the projecting elements are configured to engage the corresponding depressions of the housing.

12. The device of claim 11, wherein the first and second electrical contacts are arranged on opposite sides of the base portion.

13. The device of claim 11, wherein the reusable component further comprises an identifiable insignia, and the identifiable insignia is positioned on a surface of the reusable component facing the disposable component when the reusable component is attached to the disposable component.

14. The device of claim 11, wherein the reusable component further comprises an identifiable insignia, and the identifiable insignia comprises a communication channel I/O address.

* * * * *

UNITED STATES PATENT AND TRADEMARK OFFICE
CERTIFICATE OF CORRECTION

PATENT NO.         : 9,439,566 B2
APPLICATION NO.    : 13/841797
DATED              : September 13, 2016
INVENTOR(S)        : Arne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this
Twenty-fifth Day of September, 2018

Andrei Iancu
*Director of the United States Patent and Trademark Office*